US011627939B2

(12) United States Patent
Park et al.

(10) Patent No.: US 11,627,939 B2
(45) Date of Patent: Apr. 18, 2023

(54) WIRELESS ULTRASOUND PROBE AND ULTRASOUND IMAGING APPARATUS CONNECTED WITH WIRELESS ULTRASOUND PROBE

(71) Applicant: SAMSUNG MEDISON CO., LTD., Hongcheon-gun (KR)

(72) Inventors: Joonghyun Park, Seongnam-si (KR); Jinho Gu, Seongnam-si (KR); Donghyun Kim, Seongnam-si (KR); Gilju Jin, Seongnam-si (KR); Dukeman Hur, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 1035 days.

(21) Appl. No.: 16/226,925

(22) Filed: Dec. 20, 2018

(65) Prior Publication Data
US 2019/0239855 A1    Aug. 8, 2019

(30) Foreign Application Priority Data
Feb. 8, 2018  (KR) .................. 10-2018-0015807

(51) Int. Cl.
*A61B 8/00*    (2006.01)
*H02J 7/00*    (2006.01)
(Continued)

(52) U.S. Cl.
CPC .......... *A61B 8/4472* (2013.01); *A61B 8/4433* (2013.01); *A61B 8/4438* (2013.01);
(Continued)

(58) Field of Classification Search
CPC ... A61B 8/4472; A61B 8/4433; A61B 8/4438; A61B 8/461; A61B 8/467; A61B 8/54;
(Continued)

(56) References Cited

U.S. PATENT DOCUMENTS 6,254,540 B1 *  7/2001  Kikuchi ................ A61B 8/00
                                                600/443
8,519,998 B2 *  8/2013  Hashimoto ............ G06T 15/08
                                                345/424
(Continued)

FOREIGN PATENT DOCUMENTS

EP       3 175 794 A1    6/2017
JP       2010187833 A    9/2010
(Continued)

OTHER PUBLICATIONS

Communication dated Jul. 16, 2019 issued by the European Intellectual Property Office in counterpart European Application No. 19153782.8.
(Continued)

*Primary Examiner* — Sanjay Cattungal
(74) *Attorney, Agent, or Firm* — Sughrue Mion, PLLC

(57) ABSTRACT

Provided are a wireless ultrasound probe and an ultrasound imaging apparatus connected with the wireless ultrasound probe. The wireless ultrasound probe includes: a battery; and a charging terminal connector that is coupled to a power supply terminal of the ultrasound imaging apparatus and receives power from the power supply to charge the battery, wherein the charging terminal connector has a unique shape configured to be physically coupled to the power supply terminal.

16 Claims, 16 Drawing Sheets

(51) Int. Cl.
*G06V 40/16* (2022.01)
*G06V 40/18* (2022.01)
*G06V 40/12* (2022.01)
*G01S 7/52* (2006.01)

(52) U.S. Cl.
CPC .............. *A61B 8/461* (2013.01); *A61B 8/467* (2013.01); *A61B 8/54* (2013.01); *A61B 8/56* (2013.01); *G06V 40/1365* (2022.01); *G06V 40/172* (2022.01); *G06V 40/197* (2022.01); *H02J 7/0045* (2013.01); *A61B 8/4405* (2013.01); *A61B 8/4427* (2013.01); *A61B 8/463* (2013.01); *A61B 8/465* (2013.01); *G01S 7/52096* (2013.01)

(58) Field of Classification Search
CPC ....... A61B 8/56; A61B 8/4405; A61B 8/4427; A61B 8/463; A61B 8/465; G06K 9/00087; G06K 9/00288; G06K 9/00617; H02J 7/0045; H02J 7/0047; H02J 7/0042; G01S 7/52096
See application file for complete search history.

(56) References Cited

U.S. PATENT DOCUMENTS

| | | | |
|---|---|---|---|
| 2003/0078501 A1 | 4/2003 | Barnes et al. | |
| 2005/0203417 A1* | 9/2005 | Okuno ................ | A61B 8/0841 600/463 |
| 2006/0112033 A1* | 5/2006 | Vion ..................... | G06N 20/00 706/16 |
| 2006/0184028 A1* | 8/2006 | Wen ..................... | G01S 15/8988 600/441 |
| 2006/0241428 A1* | 10/2006 | Kao ..................... | G01S 7/52074 600/437 |
| 2007/0014446 A1* | 1/2007 | Sumanaweera ......... | G06T 15/40 382/128 |
| 2007/0167754 A1* | 7/2007 | Okuno ................ | A61B 1/0005 600/437 |
| 2008/0064955 A1 | 3/2008 | Miyajima | |
| 2008/0148393 A1* | 6/2008 | Wendt .................... | G06F 21/32 726/19 |
| 2008/0194960 A1* | 8/2008 | Randall ................ | A61B 8/4411 600/459 |
| 2008/0194961 A1* | 8/2008 | Randall .................... | A61B 8/00 600/459 |
| 2008/0194962 A1* | 8/2008 | Randall ................ | G01M 3/3272 600/459 |
| 2008/0194963 A1* | 8/2008 | Randall ................ | A61B 8/4472 600/459 |
| 2008/0194964 A1* | 8/2008 | Randall .................... | A61B 8/56 600/459 |
| 2009/0124907 A1* | 5/2009 | Bruce .................. | A61B 5/7264 600/458 |
| 2010/0022880 A1* | 1/2010 | Sathyanarayana ....... | A61B 8/12 600/443 |
| 2010/0056924 A1* | 3/2010 | Powers .................. | A61B 8/481 600/458 |
| 2010/0160786 A1 | 6/2010 | Nordgren et al. | |
| 2011/0162673 A1* | 7/2011 | Samain ................ | A45D 44/005 132/317 |
| 2012/0128218 A1* | 5/2012 | Amyot .................... | G06T 19/00 382/128 |
| 2012/0245465 A1* | 9/2012 | Hansegard ............ | A61B 8/483 600/443 |
| 2013/0109973 A1 | 5/2013 | Kurokawa | |
| 2013/0182926 A1* | 7/2013 | Lee ......................... | G06T 5/008 382/131 |
| 2014/0073925 A1* | 3/2014 | Kho ........................ | A61B 8/466 600/443 |
| 2014/0088420 A1 | 3/2014 | Lindahl | |
| 2014/0180110 A1 | 6/2014 | Schmedling | |
| 2015/0245823 A1* | 9/2015 | Jin ........................ | A61B 8/5207 600/443 |
| 2016/0199028 A1 | 7/2016 | Jeon et al. | |
| 2017/0179774 A1 | 6/2017 | Jin et al. | |

FOREIGN PATENT DOCUMENTS

| | | |
|---|---|---|
| JP | 2013126599 A | 6/2013 |
| KR | 10-1031506 B1 | 4/2011 |
| WO | 2015/009635 A1 | 1/2015 |
| WO | 2017/009735 A1 | 1/2017 |

OTHER PUBLICATIONS

Communication dated Feb. 13, 2023 issued by the Korean Patent Office in application No. 10-2018-0015807.

* cited by examiner

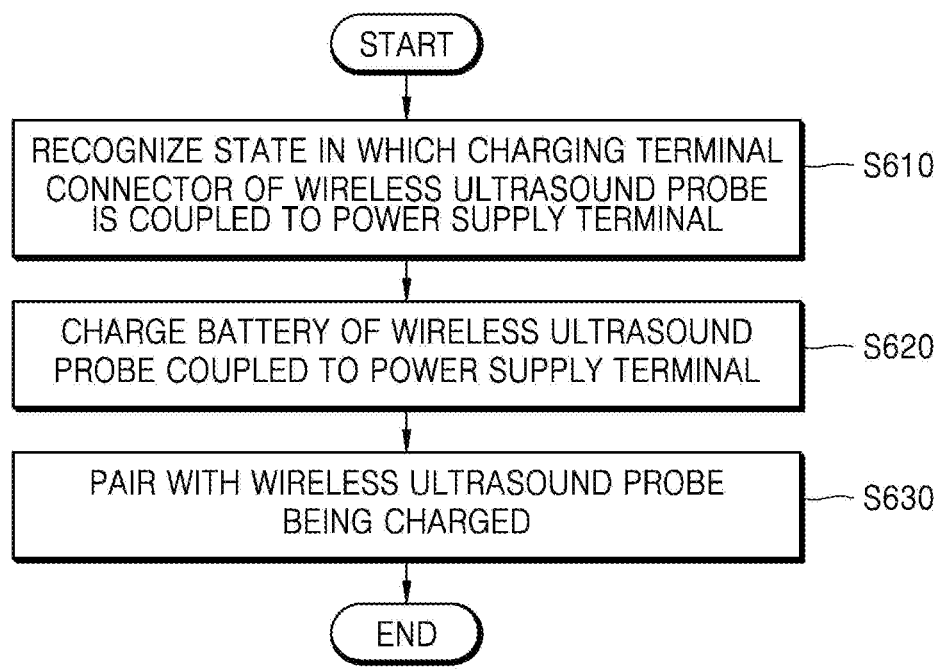

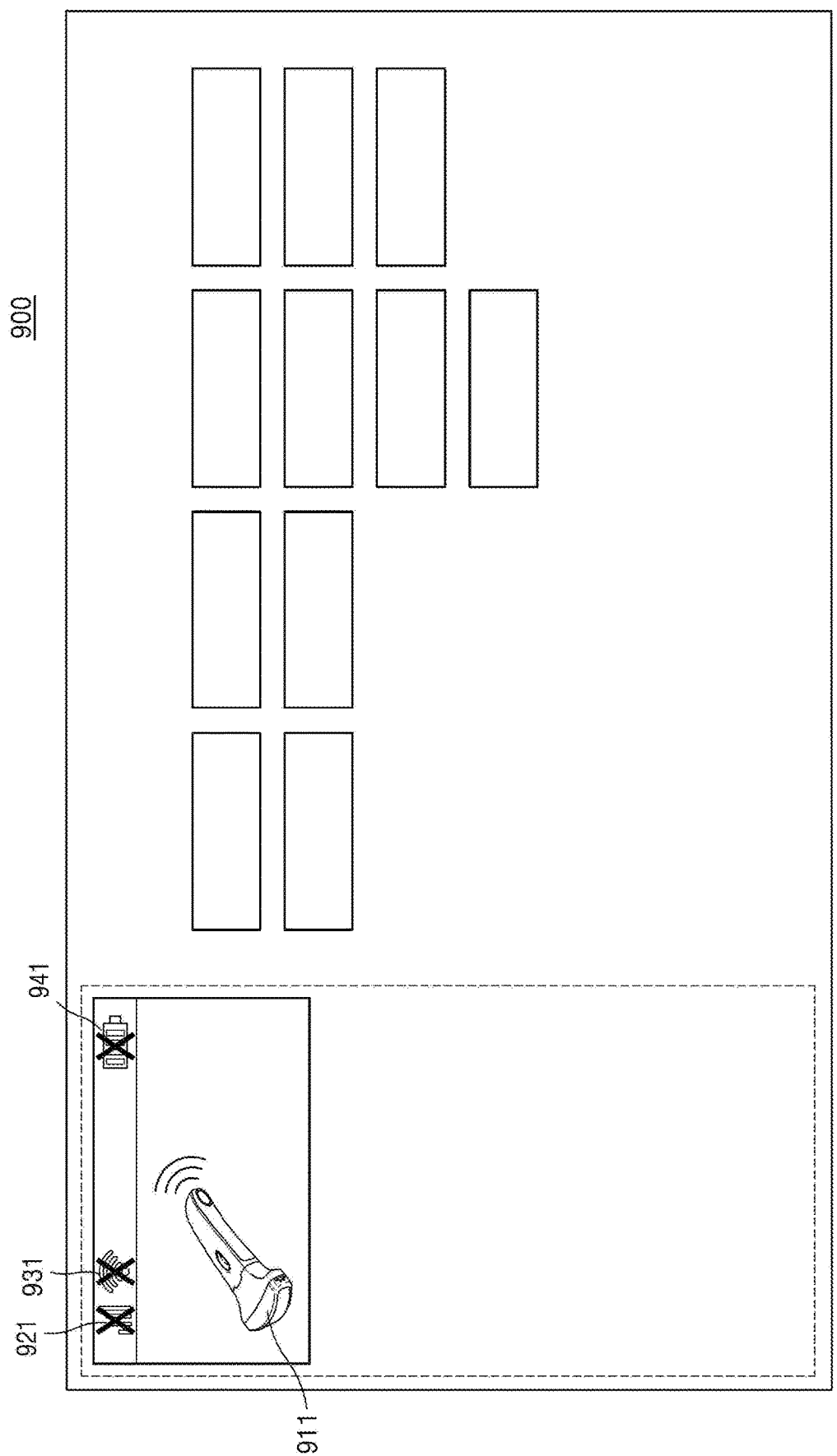

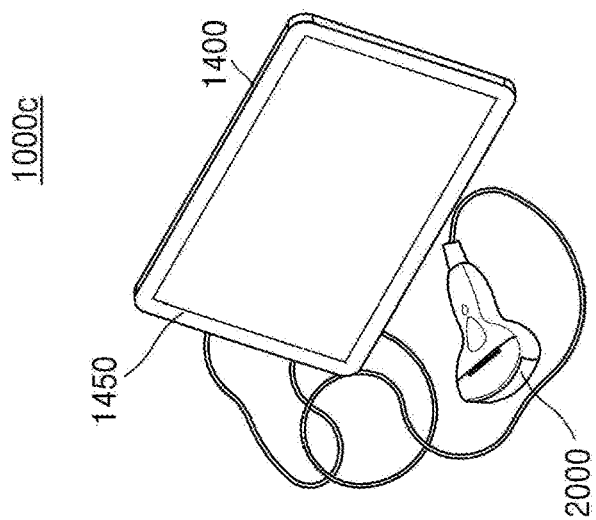
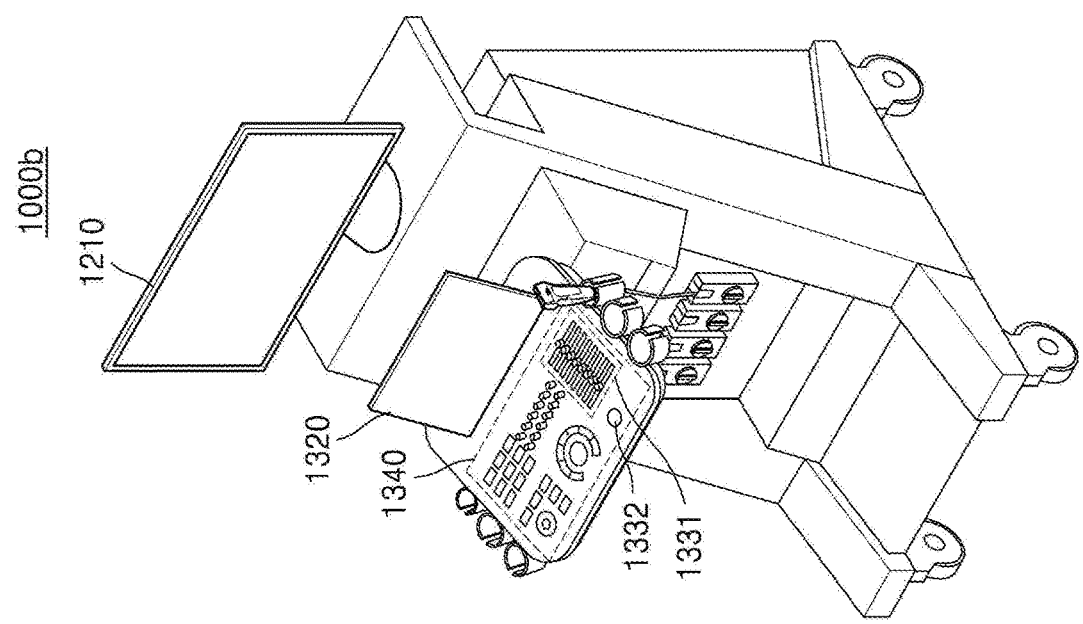
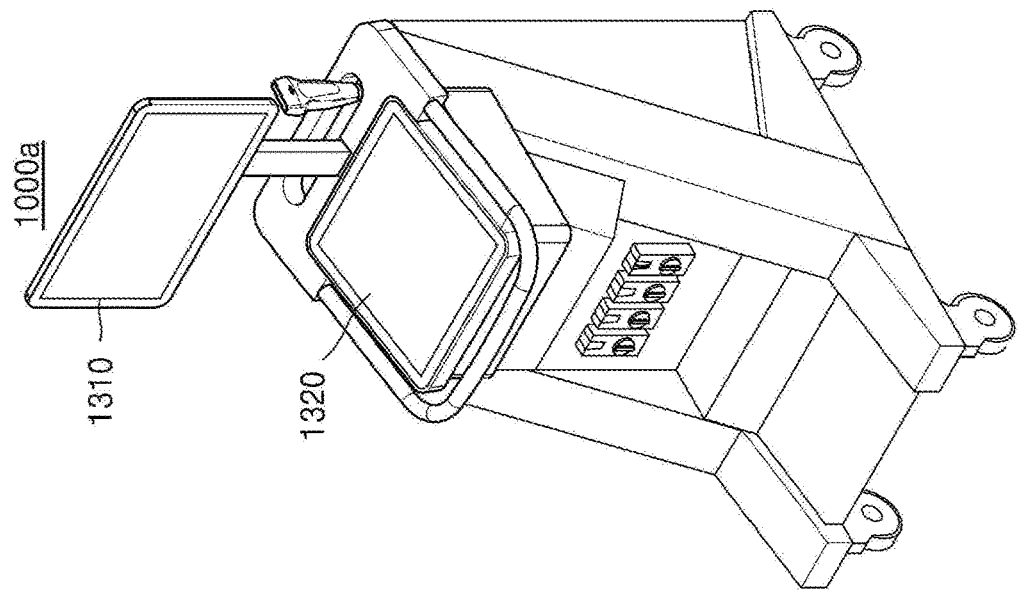
FIG. 11A
FIG. 11B
FIG. 11C

WIRELESS ULTRASOUND PROBE AND ULTRASOUND IMAGING APPARATUS CONNECTED WITH WIRELESS ULTRASOUND PROBE

CROSS-REFERENCE TO RELATED APPLICATION(S)

This application is based on and claims priority under 35 U.S.C. § 119 to Korean Patent Application No. 10-2018-0015807, filed on Feb. 8, 2018, in the Korean Intellectual Property Office, the disclosure of which is incorporated by reference herein in its entirety.

BACKGROUND

1. Field

The disclosure relates to wireless ultrasound probes and ultrasound imaging apparatuses connected with the wireless ultrasound probes, and more particularly, to wireless ultrasound probes including a physical coupling device having a unique shape for theft prevention and ultrasound imaging apparatuses that are connected with the wireless ultrasound probes and supply a charging power thereto.

2. Description of Related Art

Ultrasound systems transmit ultrasound signals generated by transducers of an ultrasound probe to an internal part of an object and receive information about echo signals reflected therefrom, thereby obtaining an image of the internal part of the object. In particular, ultrasound systems are used for medical purposes including observation of an internal area of an object, detection of foreign substances, diagnosis of damage to the object, and imaging of characteristics.

Wireless ultrasound probes connected to an ultrasound imaging apparatus by using wireless communication are nowadays being developed in order to improve the operability of an ultrasound probe by removing a communication cable for transmitting and receiving ultrasound image data between the ultrasound probe and the ultrasound imaging apparatus or by eliminating space limitations and inconvenience due to the presence of the communication cable. However, wireless ultrasound probes are easily portable without cables but are vulnerable to theft due to this cable-free structure. In particular, anti-theft technology is urgently needed for high-cost wireless ultrasound probes integrated with cutting-edge technologies.

SUMMARY

Provided are wireless ultrasound probes including a charging terminal shaped to physically mate with a power supply terminal of an ultrasound imaging apparatus. Also, provided are ultrasound imaging apparatuses configured to supply a charging power only to a wireless ultrasound probe including a charging terminal shaped to be physically coupled with a power supply terminal among wireless ultrasound probes.

Additional aspects will be set forth in part in the description which follows and, in part, will be apparent from the description, or may be learned by practice of the presented embodiments.

In accordance with an aspect of the disclosure, a wireless ultrasound probe includes: a battery; and a charging terminal connector that is coupled to a power supply terminal of the ultrasound imaging apparatus and receives power from the power supply terminal to charge the battery, wherein the charging terminal connector has a unique shape configured to be physically coupled to the power supply terminal.

For example, the charging terminal connector may have a shape corresponding to a shape of the power supply terminal such that the charging terminal connector is coupled only to the predetermined power supply terminal of the ultrasound imaging apparatus.

The charging terminal connector may include a plurality of pins coupled to the power supply terminal and may be pin mapped such that at least one of the plurality of pins receives power from the power supply terminal.

The charging terminal connector may be pin mapped to have a combination of at least two of the plurality of pins via which the power is received from the power supply terminal.

The wireless ultrasound probe may further include: a wireless communication module; and a controller configured to recognize a battery charging state in which the charging terminal connector is physically coupled to the power supply terminal such that power is applied to the battery and control, when the wireless ultrasound probe is in the battery charging state, the wireless communication module to be paired wirelessly to the ultrasound imaging apparatus by using a wireless communication method.

The wireless ultrasound probe may further include a biometric recognition module configured to acquire biometric information including at least one of a user's fingerprint, iris, and facial contour, and the controller may be further configured to identify the user based on the biometric information acquired by the biometric recognition module and control the wireless communication module to be paired with the ultrasound imaging apparatus by using a wireless communication method according to the identified user.

In accordance with another aspect of the disclosure, an ultrasound imaging apparatus includes: a wireless communication module; a power supply terminal that is coupled to a charging terminal connector of the wireless ultrasound probe to supply a charging power for charging a battery of the wireless ultrasound probe; a sensor configured to recognize a charging state in which the power supply terminal is physically coupled with the charging terminal connector of the wireless ultrasound probe such that power is supplied to the battery; and a controller configured to control the wireless communication module to pair the ultrasound imaging apparatus with the wireless ultrasound probe that is recognized by the sensor as being in the charging state by using a wireless communication method, wherein the power supply terminal has a unique shape configured to be physically coupled only to the wireless ultrasound probe.

For example, the ultrasound imaging apparatus may further include a user input interface configured to receive a password or a specific pattern from a user, and the controller may be further configured to determine, when the charging state is recognized, whether to pair the ultrasound imaging apparatus with the wireless ultrasound probe based on the received password or specific pattern.

The controller may be further configured to control the wireless communication module to receive identification (ID) information and characteristic information of the wireless ultrasound probe coupled to the power supply terminal and determine whether to pair the ultrasound imaging apparatus with the wireless ultrasound probe based on the received ID information and characteristic information of the wireless ultrasound probe.

The ultrasound imaging apparatus may further include a display configured to display a user interface (UI) indicating the charging state of the wireless ultrasound probe and a state of pairing with the wireless ultrasound probe.

The power supply terminal may include a plurality of pins and may be pin mapped such that at least one of the plurality of pins supplies power to the wireless ultrasound probe via the charging terminal connector. The sensor may be further configured to recognize whether pin mapping of the power supply terminal matches pin mapping of the charging terminal connector, and the controller may be further configured to determine whether to pair the ultrasound imaging apparatus with the wireless ultrasound probe, based on a result of the recognizing by the sensor as to whether the pin mapping of the power supply terminal matches the pin mapping of the charging terminal connector.

The controller may be further configured to prevent the power supply terminal from supplying power to the wireless ultrasound probe when the pin mapping of the power supply terminal does not match the pin mapping of the charging terminal connector.

The ultrasound imaging apparatus may further include a display configured to display a UI indicating a state in which the power is prevented from being supplied to the wireless ultrasound probe.

In accordance with another aspect of the disclosure, a method of connecting an ultrasound imaging apparatus with a wireless ultrasound probe includes: recognizing a state in which a charging terminal connector of the wireless ultrasound probe is coupled to a power supply terminal of the ultrasound imaging apparatus; supplying a power to the wireless ultrasound probe coupled to the power supply terminal to charge a battery of the wireless ultrasound probe; and pairing the ultrasound imaging apparatus with the wireless ultrasound probe being charged by using a wireless communication method.

For example, the power supply terminal may have a unique shape configured to be physically coupled only with the wireless ultrasound probe including the charging terminal connector having a predetermined shape.

The method may further include receiving a password or a specific pattern from a user, and the pairing of the ultrasound imaging apparatus with the wireless ultrasound probe may include determining, based on the received password or specific pattern, whether to pair the ultrasound imaging apparatus with the wireless ultrasound probe being charged.

The method may further include receiving identification information and characteristic information of the wireless ultrasound probe being charged, and the pairing of the ultrasound imaging apparatus with the wireless ultrasound probe may include determining whether to pair the ultrasound imaging apparatus with the wireless ultrasound probe based on the received ID information and characteristic information of the wireless ultrasound probe.

The method may further include acquiring biometric information including at least one of a fingerprint, an iris, and a facial contour of a user of the wireless ultrasound probe, and the pairing of the ultrasound imaging apparatus with the wireless ultrasound probe may include: identifying the user based on the acquired biometric information; and determining whether to pair the ultrasound imaging apparatus with the wireless ultrasound probe according to the identified user.

The method may further include displaying a UI indicating a state in which the wireless ultrasound probe is being charged and a state in which the wireless ultrasound probe is paired with the ultrasound imaging apparatus.

The method may further include: recognizing whether pin mapping of the power supply terminal matches pin mapping of the charging terminal connector; preventing the power from being supplied to the wireless ultrasound probe when the pin mapping of the power supply terminal does not match the pin mapping of the charging terminal connector; and displaying a UI indicating a state in which the power is prevented from being supplied to the wireless ultrasound probe.

BRIEF DESCRIPTION OF THE DRAWINGS

The above and other aspects, features, and advantages of certain embodiments of the present disclosure will be more apparent from the following description taken in conjunction with the accompanying drawings in which:

FIG. 6 is a flowchart of a method, performed by an ultrasound imaging apparatus, of pairing with a wireless ultrasound probe, according to an embodiment;

FIGS. 9A and 9B are diagrams for explaining methods by which an ultrasound imaging apparatus displays states of pairing with wireless ultrasound probes, according to embodiments;

FIGS. 11A through 11C are diagrams illustrating ultrasound imaging apparatuses according to embodiments.

DETAILED DESCRIPTION

Figure 1:
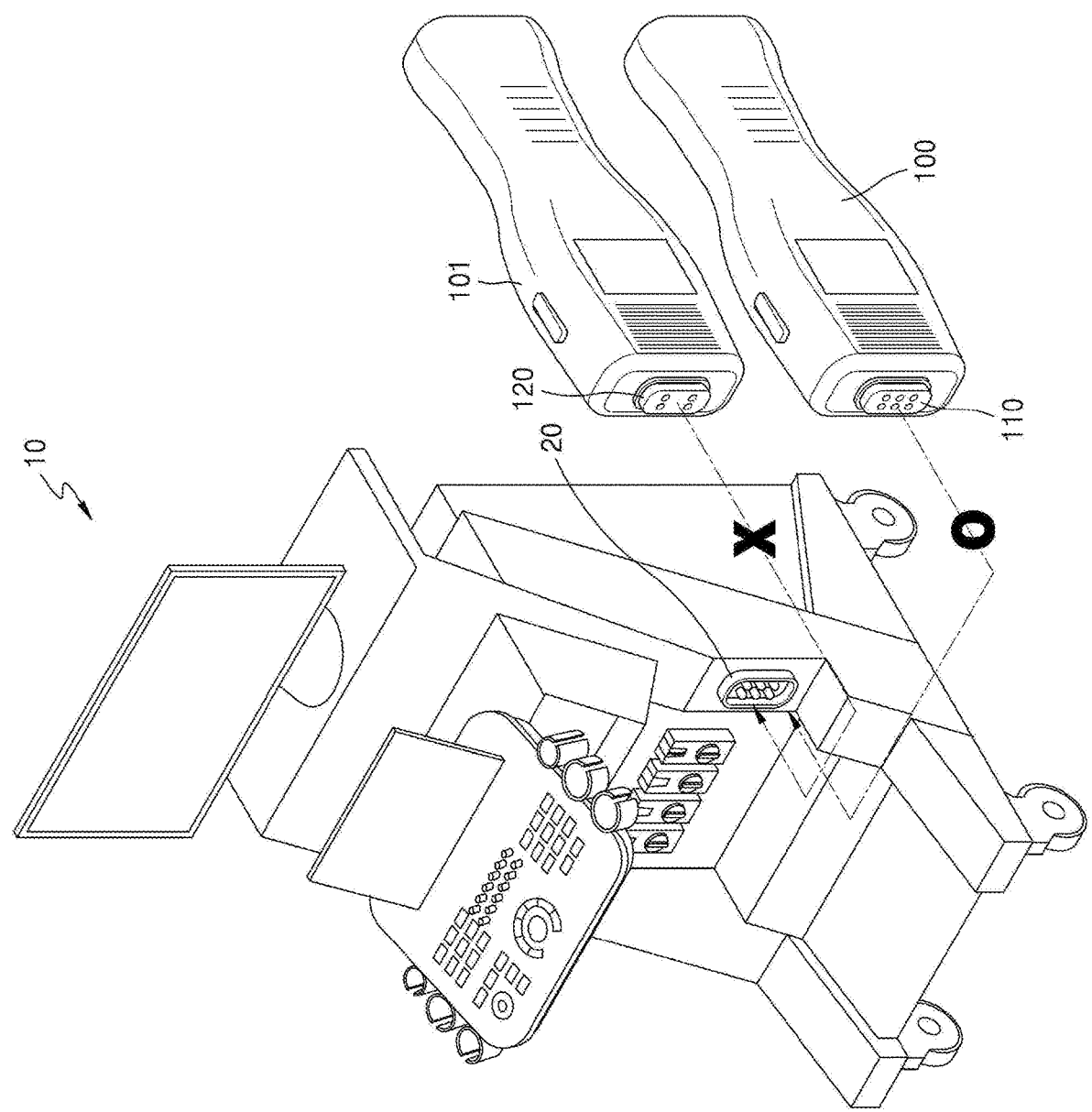
FIG. 1 is a conceptual diagram illustrating an example in which wireless ultrasound probes are each coupled to a power supply terminal of an ultrasound imaging apparatus to receive a charging power from the ultrasound imaging apparatus, according to an embodiment.

Advantages and features of one or more embodiments of the present disclosure and methods of accomplishing the same may be understood more readily by reference to the following detailed description of the embodiments and the accompanying drawings. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present disclosure will only be defined by the appended claims.

Terms used herein will now be briefly described and then one or more embodiments of the present disclosure will be described in detail.

All terms including descriptive or technical terms which are used herein should be construed as having meanings that are obvious to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description of the disclosure. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the embodiments of the present disclosure means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Expressions such as "at least one of," when preceding a list of elements, modify the entire list of elements and do not modify the individual elements of the list.

In the present specification, an "object" may be a human, an animal, or a part of a human or animal. For example, the object may be an organ (e.g., the liver, the heart, the womb, the brain, a breast, or the abdomen), a blood vessel, or a combination thereof. Furthermore, the "object" may be a phantom. The phantom means a material having a density, an effective atomic number, and a volume that are approximately the same as those of an organism. For example, the phantom may be a spherical phantom having properties similar to the human body.

Furthermore, in the present specification, a "user" may be, but is not limited to, a medical expert, such as a medical doctor, a nurse, a medical laboratory technologist, and a technician who repairs an ultrasound imaging apparatus.

Furthermore, in the present specification, the terms "first", "second", "1-1", etc. are only used to distinguish one component, element, object, image, pixel, or patch from another component, element, object, image, pixel, or patch. Thus, these terms are not limited to representing the order or priority among elements or components.

Reference will now be made in detail to embodiments, examples of which are illustrated in the accompanying drawings. In this regard, the present embodiments may have different forms and should not be construed as being limited to the descriptions set forth herein. In the following description, well-known functions or constructions are not described in detail so as not to obscure the embodiments with unnecessary detail.

FIG. 1 is a conceptual diagram illustrating an example in which first and second wireless ultrasound probes 100 and 101 are each coupled to a power supply terminal 20 of an ultrasound imaging apparatus 10 to receive a charging power from the ultrasound imaging apparatus 10, according to an embodiment Although FIG. 1 shows that the ultrasound imaging apparatus 10 is a cart type apparatus, it may also be implemented as a portable type apparatus. Examples of portable ultrasound imaging apparatuses may include, but are not limited to, a picture archiving and communication system (PACS) viewer, a hand-carried cardiac ultrasound (HCU) device, a smartphone, a laptop computer, a personal digital assistant (PDA), and a tablet PC. The ultrasound imaging apparatus 10 may be an apparatus configured to generate an ultrasound image by processing ultrasound image data received from either of the first and second wireless ultrasound probes 100 and 101 and display the generated image, or may be an apparatus for implementing only an image display function without performing a separate image processing function.

For example, the ultrasound imaging apparatus 10 may include a power supply terminal 20 configured to supply power to the first wireless ultrasound probe 100 and charge a battery of the first wireless ultrasound probe 100. In an embodiment, the power supply terminal 20 may be coupled with a first charging terminal connector 110 to charge the battery of the first wireless ultrasound probe 100.

The first and second wireless ultrasound probes 100 and 101 may each transmit ultrasound signals to an object and receive echo signals reflected from the object to thereby produce reception signals. The first and second wireless ultrasound probes 100 and 101 may each perform image processing on the reception signals to thereby generate ultrasound image data and then transmit the generated ultrasound image data to the ultrasound imaging apparatus 10.

The first and second wireless ultrasound probes 100 and 101 may respectively include first and second charging terminal connectors 110 and 120 configured to receive power from the power supply terminal 20 to charge batteries of the first and second wireless ultrasound probes 100 and 101. The first and second charging terminal connectors 110 and 120 may each have a unique shape enabling them to be_physically coupled to the power supply terminal 20. In other words, the first and second charging terminal connectors 110 and 120 may each have a shape corresponding to that of the power supply terminal 20 of the ultrasound imaging apparatus 10, such that they are each coupled only to the predetermined power supply terminal 20. In this case, "coupled" may refer to engaging a terminal having an protruding structure with an opening having a shape corresponding to the protruding structure while the terminal and the opening are in contact with each other. For example, a coupling relationship may mean a structure in which a terminal and an opening may be aligned and mated with each other as male and female elements.

In the embodiment shown in FIG. 1, the first charging terminal connector 110 attached to the first wireless ultrasound probe 100 may have a structure corresponding to that of the power supply terminal 20 such that the first charging terminal connector 110 may be coupled to the power supply terminal 20. For example, the power supply terminal 20 may include six (6) protruding terminals for supplying power, and the first charging terminal connector 110 may include the same number of openings, i.e., six (6) openings at respective positions corresponding to those of the six terminals included in the power supply terminal 20.

On the other hand, the second charging terminal connector 120 attached to the second wireless ultrasound probe 101 may not have a shape corresponding to that of the power supply terminal 20, and thus, may not be coupled to the power supply terminal 20. In other words, the second charging terminal connector 120 may be formed to have a structure that that does not enable physical coupling with the power supply terminal 20. For example, the second charging terminal connector 120 may include only a total of four (4) openings at positions that do not correspond to those of the six terminals in the power supply terminal 20. However, the shape of the second charging terminal connector 120 is merely an example, and is not limited to that shown in FIG. 1.

The ultrasound imaging apparatus 10 may supply a charging power to the first wireless ultrasound probe 100 coupled thereto via the power supply terminal 20 and may be paired with the first wireless ultrasound probe 100 by using a wireless communication method. In this case, "paired" may mean a state in which the ultrasound imaging apparatus 10 may be connected wirelessly with the first wireless ultrasound probe 100 by using a wireless communication method. In detail, pairing may refer to a method whereby the first wireless ultrasound probe 100 transmits, to the ultrasound imaging apparatus 10, information including at least one of its own identification (ID) information, a probe type, a communication method used for wireless connection, a wireless communication frequency, an executable application, battery charging information, a remaining battery capacity, and a remaining usability time, while the ultrasound imaging apparatus 10 wirelessly connects with the first wireless ultrasound probe 100 based on the received information.

"Pairing" is conceptually different from "activation". "Activation" may be defined as a state in which the ultrasound imaging apparatus 10 transmits a control signal such as a power control signal or a beamforming control signal to the first wireless ultrasound probe 100 and is able to operate the first wireless ultrasound probe 100 to transmit ultrasound signals to the object, receive ultrasound echo signals reflected from the object, or transmit ultrasound image data generated by the first wireless ultrasound probe 100 itself to the ultrasound imaging apparatus 10.

In an embodiment, when the ultrasound imaging apparatus 10 recognizes that a charging power is being applied to the first wireless ultrasound probe 100, the ultrasound imaging apparatus 10 may transmit a pairing signal only to the first wireless ultrasound probe 100 being charged. In other words, the ultrasound imaging apparatus 10 may pair only with the first wireless ultrasound probe 100 and not with the second wireless ultrasound probe 101. In other words, since a connection for supplying a charging power is not simply for charging a wireless ultrasound probe, the wireless ultrasound probe requires a connection to the power supply terminal 20 for supplying a charging power even when the wireless ultrasound probe is fully charged.

The first and second wireless ultrasound probes 100 and 101 are designed to eliminate space limitations and improve operability of an ultrasound probe by removing cables, as compared to a wired ultrasound probe of the related art connected to the ultrasound imaging apparatus 10 via a communication cable to perform data communication. However, the first and second wireless ultrasound probes 100 and 101 are vulnerable to theft because they do not include cables. In particular, anti-theft technology is urgently needed for high-cost wireless ultrasound probes integrated with cutting-edge technologies.

According to the embodiment shown in FIG. 1, the first wireless ultrasound probe 100 includes the first charging terminal connector 110 having a unique shape that enables it to be physically coupled only to the predetermined power supply terminal 20 of the ultrasound imaging apparatus 10. On the other hand, the second wireless ultrasound probe 101 has attached thereto the second charging terminal connector 120 with a shape that cannot be physically coupled to the power supply terminal 20 of the ultrasound imaging apparatus 10. Since it is impossible to wirelessly charge a battery of the second wireless ultrasound probe 120 or to wirelessly pair therewith, this may weaken a thief's desire for stealing the second wireless ultrasound probe 120. In other words, it is meaningless and of no benefit to steal the second wireless ultrasound probe 120 with respect to which battery charging or wireless pairing is not possible even when it is stolen.

Referring to FIG. 1, the first wireless ultrasound probe 100 includes the first charging terminal connector 110 having a structure capable of physically coupling with the power supply terminal 20, whereas the second wireless ultrasound probe 101 includes the second charging terminal connector 120 having a completely different shape than that of the power supply terminal 20 so as not to physically mate with the power supply terminal 20. However, embodiments are not limited thereto. In other words, even when a charging terminal connector of a wireless ultrasound probe is capable of being physically coupled to the power supply terminal 20, pins arranged in the charging terminal connector may be mapped differently than in the power supply terminal 20, such that charging cannot be performed. Mapping between a charging terminal connector and a power supply terminal will be described in more detail below with reference to FIGS. 3A and 3B.

Figure 2A:
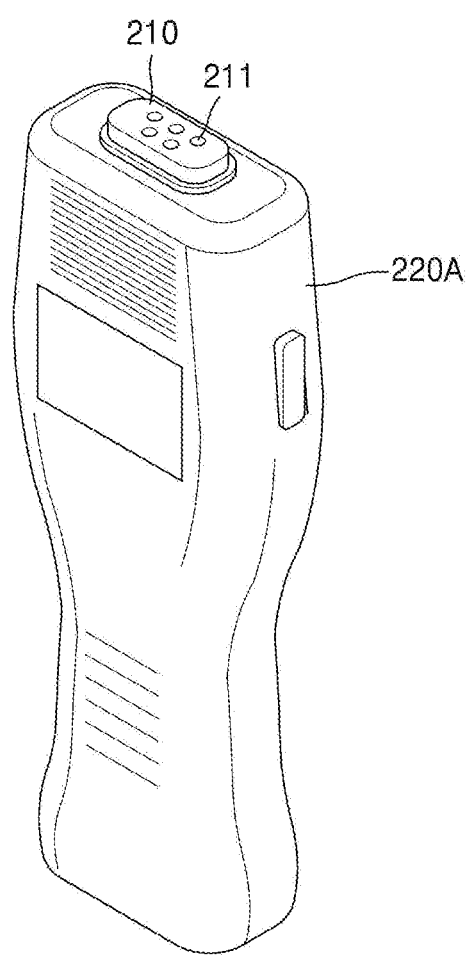
FIGS. 2A and 2B are perspective views of charging terminal connectors of wireless ultrasound probes according to embodiments.
Figure 2B:
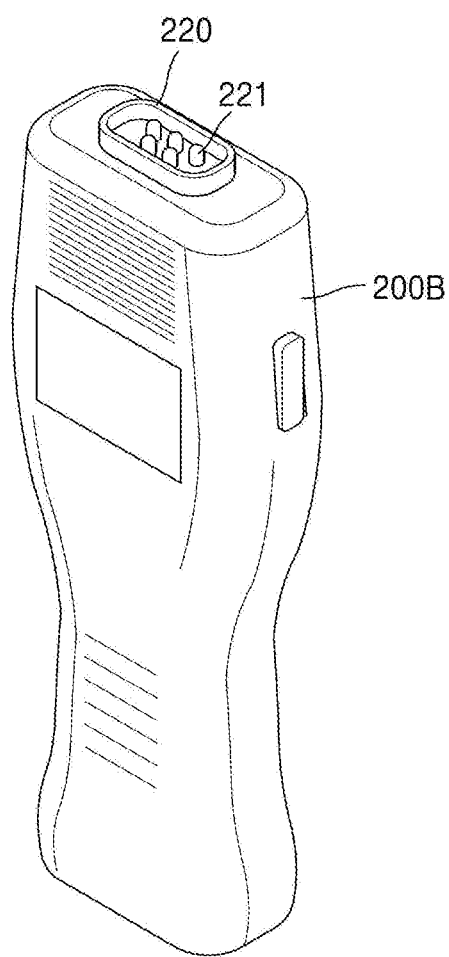

FIGS. 2A and 2B are respectively perspective views of charging terminal connectors of wireless ultrasound probes 200A and 200B according to embodiments.

Referring to FIG. 2A, a charging terminal connector 210 may be provided on one side of the wireless ultrasound probe 200A. The charging terminal connector 210 may receive a charging power for charging a battery from the power supply terminal (20 of FIG. 1) of the ultrasound imaging apparatus (10 of FIG. 1). The charging terminal connector 210 may have a shape corresponding to that of the power supply terminal 20 of the ultrasound imaging apparatus 10 such that the charging terminal connector 210 may be physically coupled only to the predetermined power supply terminal 20.

According to an embodiment, the charging terminal connector 210 may have a structure including a plurality of openings 211 formed in a direction toward the wireless ultrasound probe 200A, i.e., the inside thereof. For example, the charging terminal connector 210 may include a total of five (5) openings 211. The plurality of openings 211 may be spaced apart from one another by a predetermined distance. The number and a size (diameter) of and a separation distance between the plurality of openings 211 in the charging terminal connector 210 may respectively correspond to the number and a size of and a separation distance between a plurality of terminals in the power supply terminal 20 of the ultrasound imaging apparatus 10. The number, size, and shape of and separation distance between the plurality of openings 211 in the charging terminal connector 210 shown in FIG. 2A are merely an example and are not limited to those shown in FIG. 2A.

Referring to FIG. 2B, a charging terminal connector 220 may be provided on one side of the wireless ultrasound probe 200B. The charging terminal connector 220 may have a shape corresponding to that of the power supply terminal 20 of the ultrasound imaging apparatus 10 to be physically coupled only to the power supply terminal 20.

In an embodiment, the charging terminal connector 220 may include a plurality of terminals 221 protruding outwards. For example, the number of the plurality of terminals 221 may be five (5), but is not limited thereto. The plurality of terminals 221 may be spaced apart from one another by a predetermined distance. The plurality of terminals 221 may each have a shape corresponding to an opening in the power supply terminal 20 of the ultrasound imaging apparatus 10 so that the plurality of terminals 221 may be respectively fit into a plurality of openings in the power supply terminal 20. In other words, a diameter of each of the plurality of terminals 221 and a separation distance therebetween may respectively correspond to a diameter of and a separation distance between each of the plurality of openings in the power supply terminal 20 of the ultrasound imaging apparatus 10.

The size (diameter) of and separation distance between the plurality of terminals 221 in the charging terminal connector 220 shown in FIG. 2B are merely an example and are not limited to those shown in FIG. 2B.

According to the embodiments shown in FIGS. 2A and 2B, the wireless ultrasound probes 200A and 200B respectively include the charging terminal connectors 210 and 220 having different shapes, and the charging terminal connectors 210 and 220 may each have a shape corresponding to that of the power supply terminal 20 of the ultrasound imaging apparatus 10 such that they are each coupled only to the predetermined power supply terminal 20. This configuration may make battery charging impossible even if the wireless ultrasound probes 200A and 200B are stolen and used and thus weaken or eliminate the inclination to steal, thereby preventing the wireless ultrasound probes 200A and 200B from being stolen.

Figure 3A:
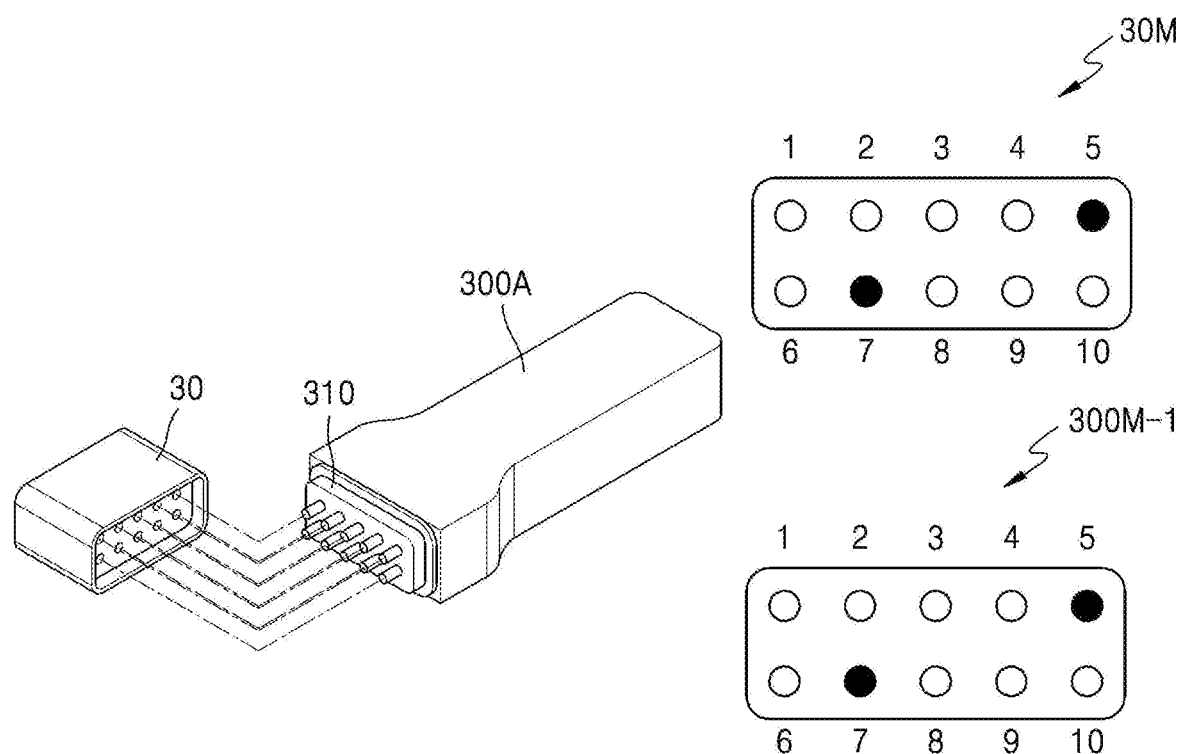
FIGS. 3A and 3B are conceptual diagrams illustrating methods of respectively coupling charging terminal connectors of wireless ultrasound probes to a power supply terminal, according to embodiments.
Figure 3B:
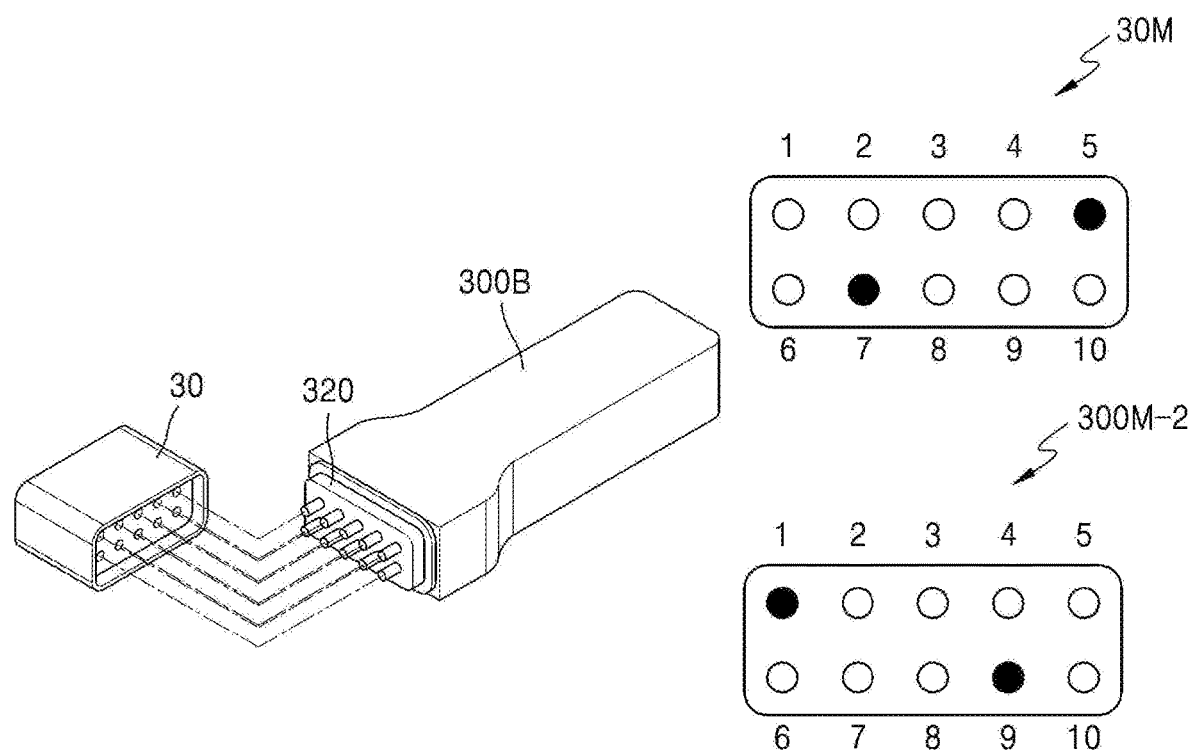

FIGS. 3A and 3B are conceptual diagrams illustrating methods of respectively coupling charging terminal connectors 310 and 320 of wireless ultrasound probes 300A and 300B to a power supply terminal 30, according to embodiments.

Referring to FIG. 3A, the charging terminal connector 310 of the wireless ultrasound probe 300A may be coupled to the power supply terminal 30 of an ultrasound imaging apparatus. In an embodiment, the charging terminal connector 310 may include a plurality of pins. The charging terminal connector 310 may include the same number of pins as that of a plurality of openings in the power supply terminal 30. A diameter of each of the plurality of pins and a separation distance therebetween may respectively correspond to a diameter of and a separation distance between the plurality of openings in the power supply terminal 30.

The charging terminal connector 310 may be pin mapped so that at least one of the plurality of pins included therein may receive power from the power supply terminal 30. In an embodiment, only at least one of the plurality of openings in the power supply terminal 30 may supply power to the at least one of the plurality of pins in the charging terminal connector 310. In this case, pin mapping may refer to mapping such that power is transmitted or received via a combination of at least one of the plurality of pins or openings or at least two of the plurality of pins or openings.

The power supply terminal 30 and the charging terminal connector 310 may be respectively mapped according to preset pin maps 30M and 300M-1. For example, referring to the pin map 30M of the power supply terminal 30, the power supply terminal 30 may be mapped to supply a charging power to the wireless ultrasound probe 300A via fifth and seventh openings among the plurality of openings. Referring to the pin map 300M-1 of the charging terminal connector 310 of the wireless ultrasound probe 300A, the charging terminal connector 310 may also be mapped to receive a charging power from the power supply terminal 30 via fifth and seventh pins. In the embodiment shown in FIG. 3A, the pin map 300M-1 of the charging terminal connector 310 of the wireless ultrasound probe 300A is identical to the pin map 30M of the power supply terminal 30, and accordingly, the wireless ultrasound probe 300A may receive a charging power from the power supply terminal 30.

Referring to FIG. 3B, the charging terminal connector 320 of the wireless ultrasound probe 300B may be coupled to the power supply terminal 30. Similarly to the charging terminal connector 310 described with reference to FIG. 3A, the charging terminal connector 320 may include a plurality of pins that are coupled to the power supply terminal 30. The charging terminal connector 320 may include the same number of pins as that of the plurality of openings formed in the power supply terminal 30. A diameter of and a separation distance between the plurality of pins included in the charging terminal connector 320 may respectively correspond to a diameter of and a separation distance between the plurality of openings in the power supply terminal 30.

Referring to a pin map 300M-2 of the charging terminal connector 320, the charging terminal connector 320 may receive a charging power for charging a battery of the wireless ultrasound probe 300B via first and ninth pins among the plurality of pins. On the other hand, referring to the pin map 30M of the power supply terminal 30, the power supply terminal 30 may be mapped to supply power for charging the wireless ultrasound probe 300B via the fifth and seventh openings among the plurality of openings. In other words, in the embodiment shown in FIG. 3B, the pin map 30M of the power supply terminal 30 is not identical to the pin map 300M-2 of the charging terminal connector 320 of the wireless ultrasound probe 300B.

According to the embodiment shown in FIG. 3B, since the pin map 300M-2 of the charging terminal connector 320 of the wireless ultrasound probe 300B is not identical to the pin map 30M of the power supply terminal 30, a charging power is not supplied to the wireless ultrasound probe 300B even when the wireless ultrasound probe 300B is physically coupled to the power supply terminal 30. Furthermore, when the charging power is not supplied to the wireless ultrasound probe 300B, the ultrasound imaging apparatus is not paired wirelessly with the wireless ultrasound probe 300B even when the wireless ultrasound probe 300B is physically coupled to the power supply terminal 30.

In the embodiments described with reference to FIGS. 3A and 3B, the wireless ultrasound probes 300A and 300B are respectively capable of being coupled to the power supply terminal 30, but whether the wireless ultrasound probes 300A and 300B are each to receive a charging power from the power supply terminal 30 is determined according to the pin maps 300M-1 and 300M-2. In other words, only the wireless ultrasound probe 300A that is mapped based on the same pin map as that of the power supply terminal 30 may receive a charging power from the power supply terminal 30. By setting the pin map 300M-1 of the charging terminal connector 310 of the wireless ultrasound probe 300A to be identical to the pin map 30M of the power supply terminal 30 of the ultrasound imaging apparatus, the wireless ultrasound probe 300B having the pin map 300M-2 that is not identical to the pin map 30M cannot be charged or paired wirelessly with the ultrasound imaging apparatus. Thus, this configuration may weaken or eliminate the inclination to steal.

Figure 4:
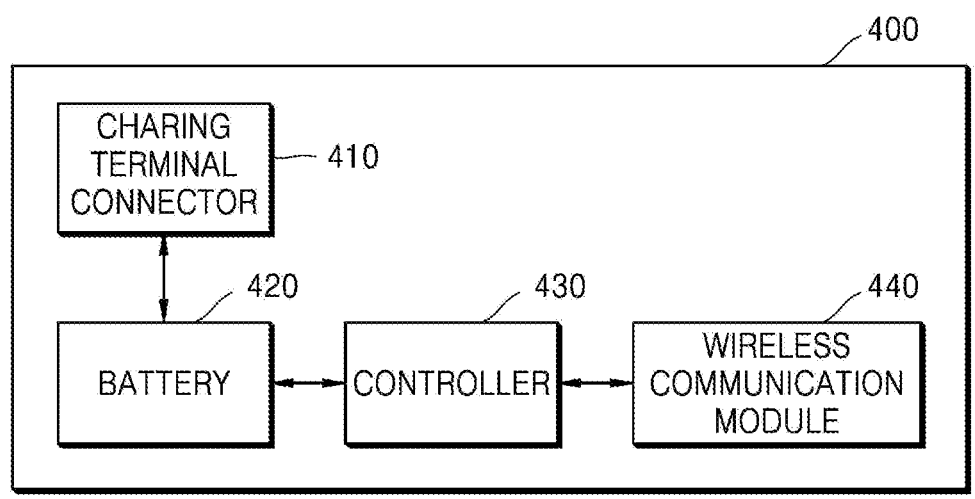
FIG. 4 is a block diagram of a configuration of a wireless ultrasound probe according to an embodiment.

FIG. 4 is a block diagram of a configuration of a wireless ultrasound probe 400 according to an embodiment. The wireless ultrasound probe 400 may transmit ultrasound signals to an object and receive echo signals reflected from the object to thereby produce reception signals. The wireless ultrasound probe 400 may also perform image processing on the reception signals to thereby generate ultrasound image data. In an embodiment, the wireless ultrasound probe 400 may transmit the generated ultrasound image data wirelessly to an ultrasound imaging apparatus.

Referring to FIG. 4, the wireless ultrasound probe 400 may include a charging terminal connector 410, a battery 420, a controller 430, and a wireless communication module 440.

The charging terminal connector 410 may be coupled to a power supply terminal of the ultrasound imaging apparatus to receive power from the power supply terminal and charge the battery 420. The charging terminal connector 410 may have a unique shape enabling it to be physically coupled to the power supply terminal. In an embodiment, the charging terminal connector 410 may have a shape corresponding to that of the power supply terminal of the ultrasound imaging apparatus, such that the charging terminal connector 410 is coupled only to the predetermined power supply terminal.

In an embodiment, the charging terminal connector 410 may include a plurality of pins that are coupled to the power supply terminal of the ultrasound imaging apparatus and may be pin mapped such that at least one of the plurality of pins included therein may receive power from the power supply terminal. In another embodiment, the charging terminal connector 410 may be pin mapped to have a combination of at least two of the plurality of pins via which power is received from the power supply terminal, and pin mapping of the charging terminal connector 410 may be identical to pin mapping of the power supply terminal.

The battery 420 may supply an operating power to the wireless ultrasound probe 400. In particular, the battery 420 may supply an operating power to the controller 430 and the wireless communication module 440. In this case, an operating power may mean a power generated by the battery 420 and supplied to perform respective functions of the controller 430 and the wireless communication module 440. The battery 420 may be a rechargeable secondary battery. The battery 420 may be a lithium ion (Li-ion) battery, but is not limited thereto. For example, the battery 420 may consist of at least one of a Li-ion battery, a Li polymer battery, a nickel (Ni)-cadmium (Cd) battery, a lead-acid battery, and a nickel metal hydride battery (NiMH).

The controller 430 may receive an operating power from the battery 420 to control the wireless communication module 440. The controller 430 may recognize a battery charging state in which the charging terminal connector 410 is physically coupled to the power supply terminal such that power is applied to the battery 420. When the wireless ultrasound probe 400 is in the battery charging state, the controller 430 may control the wireless communication module 440 to be paired wirelessly to the ultrasound imaging apparatus by using a wireless communication method.

For example, the controller 430 may be formed as a hardware module including at least one of a central processing unit (CPU), a microprocessor, a graphic processing unit (GPU), random-access memory (RAM), and read-only memory (ROM). In an embodiment, the controller 430 may be implemented as an application processor (AP). In another embodiment, the controller 430 may also be implemented as a hardware component such as a FPGA or an ASIC.

The controller 430 may control the wireless communication module 440 to wirelessly transmit ID information and characteristic information to the ultrasound imaging apparatus. In this case, the ID information may refer to an ID and a type of the wireless ultrasound probe 400, and the characteristic information may be information including at least one of a wireless communication frequency used for wireless communication with the ultrasound imaging apparatus, a connection type, an executable application, a wireless communication method, a communication status, battery charging information, a remaining battery capacity, and a remaining usability time.

The wireless communication module 440 may be paired with the ultrasound imaging apparatus by using a wireless communication method. For example, the wireless communication module 440 may be paired wirelessly to the ultrasound imaging apparatus by using at least one of wireless communication methods including a Wireless Local Area Network (WLAN), Wireless Fidelity (Wi-Fi), Bluetooth, Zigbee, Wi-Fi Direct (WFD), Infrared Data Association (IrDA), Bluetooth Low Energy (BLE), Near Field Communication (NFC), Wireless Broadband Internet (WiBro), World Interoperability for Microwave Access (WiMAX), Shared Wireless Access Protocol (SWAP), Wireless Gigabit Alliance (WiGig), and radio frequency (RF) communication.

In an embodiment, the wireless communication module 440 may include a 60-GHz millimeter wave (mmWave) data communication module configured to transmit ultrasound raw data to the ultrasound imaging apparatus. In another embodiment, the wireless communication module 440 may include only a local area communication module for pairing with the ultrasound imaging apparatus.

Although not shown in FIG. 4, the wireless ultrasound probe 400 may further include a biometric recognition module. The biometric recognition module may acquire biometric information including at least one of a user's fingerprint, iris, and facial contour. The controller 430 may identify a user based on the biometric information acquired by the biometric recognition module and control the wireless communication module 440 to be paired with the ultrasound imaging apparatus by using a wireless communication method according to the identified user, as will be described in more detail below with reference to FIG. 7C.

Figure 5:
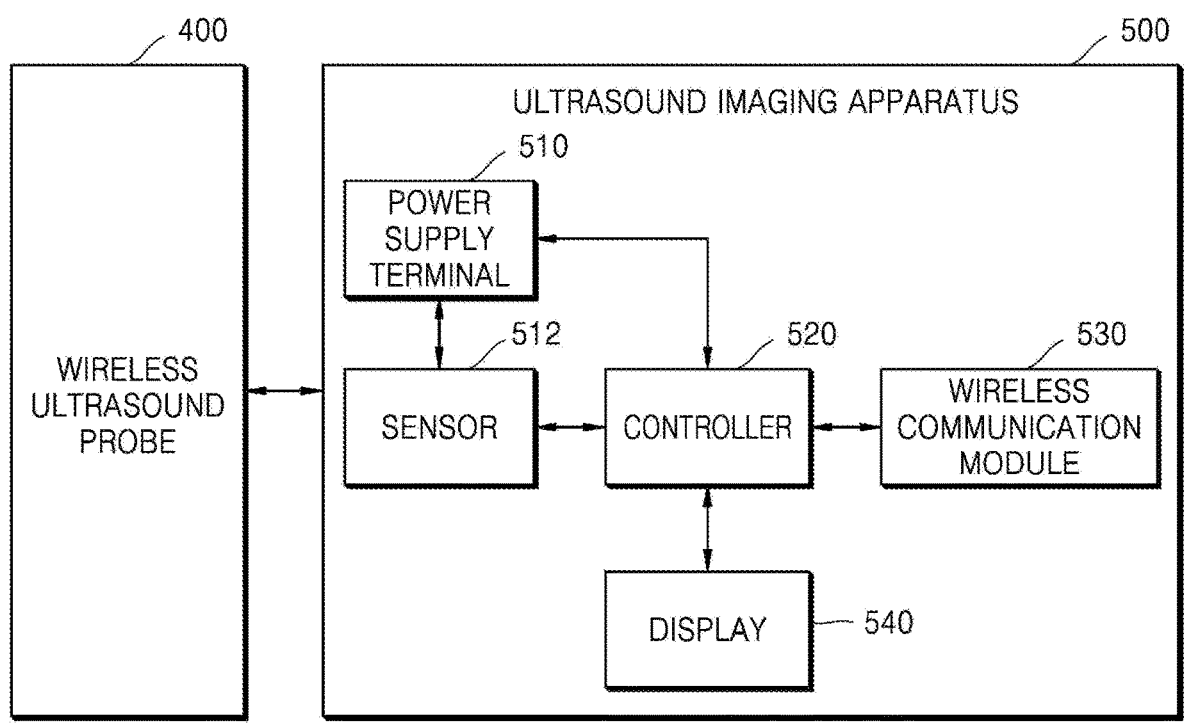
FIG. 5 is a block diagram of a configuration of an ultrasound imaging apparatus according to an embodiment.

FIG. 5 is a block diagram of a configuration of an ultrasound imaging apparatus 500 according to an embodiment. The ultrasound imaging apparatus 500 may be connected wirelessly with a wireless ultrasound probe 400. The ultrasound imaging apparatus 500 may be implemented as a cart type apparatus as well as a portable type apparatus. Examples of portable ultrasound imaging apparatuses may include, but are not limited to, a PACS viewer, a HCU device, a smartphone, a laptop computer, a PDA, and a tablet PC.

In an embodiment, the ultrasound imaging apparatus 500 may be an apparatus configured to generate an ultrasound image by processing ultrasound image data received from the wireless ultrasound probes 400 and display the generated image, or may be an apparatus for implementing only an image display function without performing a separate image processing function.

Referring to FIG. 5, the ultrasound imaging apparatus 500 may include a power supply terminal 510, a sensor 512, a controller 520, a wireless communication module 530, and a display 540.

The power supply terminal 510 may supply power to the wireless ultrasound probe 400 to charge the battery (420 of FIG. 4) of the wireless ultrasound probe 400. The power supply terminal 510 may be physically coupled with the charging terminal connector (410 of FIG. 4) of the wireless ultrasound probe 400. In an embodiment, the power supply terminal 510 may have a unique shape enabling it to be coupled only to the wireless ultrasound probe 400 including the charging terminal connector 410 having a predetermined shape.

In an embodiment, the power supply terminal 510 may include a plurality of pins and may be pin mapped such that at least one of the plurality of pins may supply a charging power to the wireless ultrasound probe 400 via the charging terminal connector 410. In another embodiment, the power supply terminal 510 may include a plurality of openings and may be pin mapped such that only at least one of the plurality of openings may supply a charging power to the wireless ultrasound probe 400 via the charging terminal connector 410. Pin mapping of the power supply terminal 510 may be identical to pin mapping of the charging terminal connector 410 of the wireless ultrasound probe 400.

The sensor 512 may recognize a charging state in which the power supply terminal 510 is physically coupled with the charging terminal connector 410 to supply power to the battery 420. In an embodiment, the sensor 512 may recognize whether the pin mapping of the power supply terminal 510 is identical to the pin mapping of the charging terminal connector 410.

In an embodiment, the sensor 512 may not only recognize a status of power connection between the power supply terminal 510 and the charging terminal connector 410 of the wireless ultrasound probe 400 but also acquire additional information. For example, even when the power supply terminal 510 of the ultrasound imaging apparatus 500 has the same physical shape as the charging terminal connector 410 of the wireless ultrasound probe 400, the power supply terminal 510 may supply a positive (+) power via three (3) terminals (e.g., terminals 1 through 3), but the charging terminal connector 410 may receive the positive (+) power via two (2) terminals (e.g., terminals 2 and 3). In this case, a charging power may be supplied to the wireless ultrasound probe 400, but the ultrasound imaging apparatus 500 is not capable of being paired with the wireless ultrasound probe 400 due to a mismatch between power terminals in the power supply terminal 510 and the charging terminal connector 410. In other words, the sensor 512 may acquire information about the number and positions of 'positive' (+) terminals via which a charging power is to be supplied.

The controller 520 may receive from the sensor 512 a state of physical mating between the power supply terminal 510 and the charging terminal connector 410 of the wireless ultrasound probe 400 and a charging state of the wireless ultrasound probe 400, and control the wireless communication module 530 such that the wireless ultrasound probe 400 in the charging state may be paired with the ultrasound imaging apparatus 500 by using a wireless communication method. In an embodiment, the controller 520 may determine whether to supply a charging power to the wireless ultrasound probe 400, based on a result of sensing by the sensor 512 as to whether pin mapping of the power supply terminal 510 is identical to pin mapping of the charging terminal connector 410. In detail, the controller 520 may control the power supply terminal 510 to supply a charging power to the wireless ultrasound probe 400 only when the pin mapping of the power supply terminal 510 is identical to the pin mapping of the charging terminal connector 410. When the sensor 512 recognizes that the pin mapping of the power supply terminal 510 is not identical to that of the charging terminal connector 410, the controller 520 may prevent the power supply terminal 510 from supplying power to the wireless ultrasound probe 400.

For example, the controller 520 may be formed as a hardware module including at least one of a CPU, a microprocessor, a GPU, RAM, and ROM. In an embodiment, when the ultrasound imaging apparatus 500 is implemented as a portable type apparatus such as a smartphone, a laptop computer, a PDA, or a tablet PC, the controller 520 the controller 520 may be implemented as an AP.

According to an embodiment, the controller 520 may control the wireless communication module 530 to receive ID information and characteristic information of the wireless ultrasound probe 400 that is coupled to the power supply terminal 510, and determine whether to pair with the wireless ultrasound probe 400 based on the ID information and the characteristic information of the wireless ultrasound probe 400. In this case, the characteristic information of the wireless ultrasound probe 400 may include at least one of a wireless communication frequency used for communication, a connection type, an executable application, a wireless communication method, a communication status, battery charging information, a remaining battery capacity, and a remaining usability time. The controller 520 may respectively compare the received ID information and characteristic information with prestored ID information and characteristic information and control the wireless communication module 530 to pair only with the wireless ultrasound probe 400 registered with the ultrasound imaging apparatus 500.

The wireless communication module 530 may be connected with the wireless ultrasound probe 400 by using a wireless communication method. For example, the wireless communication module 530 may be paired wirelessly with the wireless ultrasound probe 400 by using at least one of wireless communication methods including a WLAN, Wi-Fi, Bluetooth, Zigbee, WFD, IrDA, BLE, NFC, WiBro, WiMAX, SWAP, WiGig, and RF communication.

The display 540 may display a UI indicating a state in which the wireless ultrasound probe 400 is being charged and a state of pairing with the wireless ultrasound probe 400. In an embodiment, when the power supply terminal 510 has a different shape from the charging terminal connector 410 not to be physically coupled to the wireless ultrasound probe 400, or when power is not supplied to the wireless ultrasound probe 400 due to a mismatch between the pin mappings of the power supply terminal 510 and the charging terminal connector 410, the display 540 may display a UI indicating a state in which power is prevented from being supplied to the wireless ultrasound probe 400.

The display 540 may be constructed by a physical device including at least one of a liquid crystal display (LCD), a plasma display panel (PDP), an organic light-emitting diode (OLED) display, a field-emission display (FED), a an LED display, a vacuum fluorescent display (VFD), a digital light processing (DLP) display, a flat panel display, a three-dimensional (3D) display, and a transparent display, but embodiments are not limited thereto. According to an embodiment, the display 540 may be formed as a touch screen including a touch interface.

Although not shown in FIG. 5, the ultrasound imaging apparatus 500 may further include a user input interface for receiving a password or a specific pattern from a user. The user input interface may include hardware components such as a key pad, a mouse, a trackball, a touch pad, a touch screen, and a jog switch, but are not limited thereto. When the display 540 is formed as a touch screen, the display 540 may be integrated with a touch pad to receive a user touch input.

The controller 520 may determine whether to pair the ultrasound imaging apparatus 500 with the wireless ultrasound probe 400, based on the password or specific pattern received via the user input interface, as will be described in more detail below with reference to FIGS. 7A and 7B.

FIG. 6 is a flowchart of a method, performed by an ultrasound imaging apparatus, of pairing with a wireless ultrasound probe, according to an embodiment.

The ultrasound imaging apparatus recognizes a state in which a charging terminal connector of the wireless ultrasound probe is coupled to a power supply terminal (S610). In an embodiment, the power supply terminal of the ultrasound imaging apparatus may have a unique shape enabling it to be coupled only to the wireless ultrasound probe including the charging terminal connector with a predetermined shape. In an embodiment, the ultrasound imaging apparatus may recognize whether pin mapping of the power supply terminal is identical to pin mapping of the charging terminal connector of the wireless ultrasound probe.

The ultrasound imaging apparatus charges a battery of the wireless ultrasound probe coupled to the power supply terminal (S620). In an embodiment, the ultrasound imaging apparatus may supply a charging power to the wireless ultrasound probe only when pin mapping of the power supply terminal is identical to pin mapping of the charging terminal connector of the wireless ultrasound probe. When the ultrasound imaging apparatus recognizes that the pin mapping of the power supply terminal is not identical to the pin mapping of the charging terminal connector, the ultrasound imaging apparatus may prevent power from being supplied to the wireless ultrasound probe.

The ultrasound imaging apparatus pairs with the wireless ultrasound probe being charged by using a wireless communication method (S630). In an embodiment, the ultrasound imaging apparatus may transmit a pairing signal to the wireless ultrasound probe that is coupled to the power supply terminal and is receiving a charging power via the power supply terminal and wirelessly connect with the wireless ultrasound probe. In an embodiment, the ultrasound imaging apparatus may be paired with the wireless ultrasound probe by using at least one of wireless communication methods including a WLAN, Wi-Fi, Bluetooth, Zigbee, WFD, IrDA, BLE, NFC, WiBro, WiMAX, SWAP, WiGig, and RF communication.

Figure 7A:
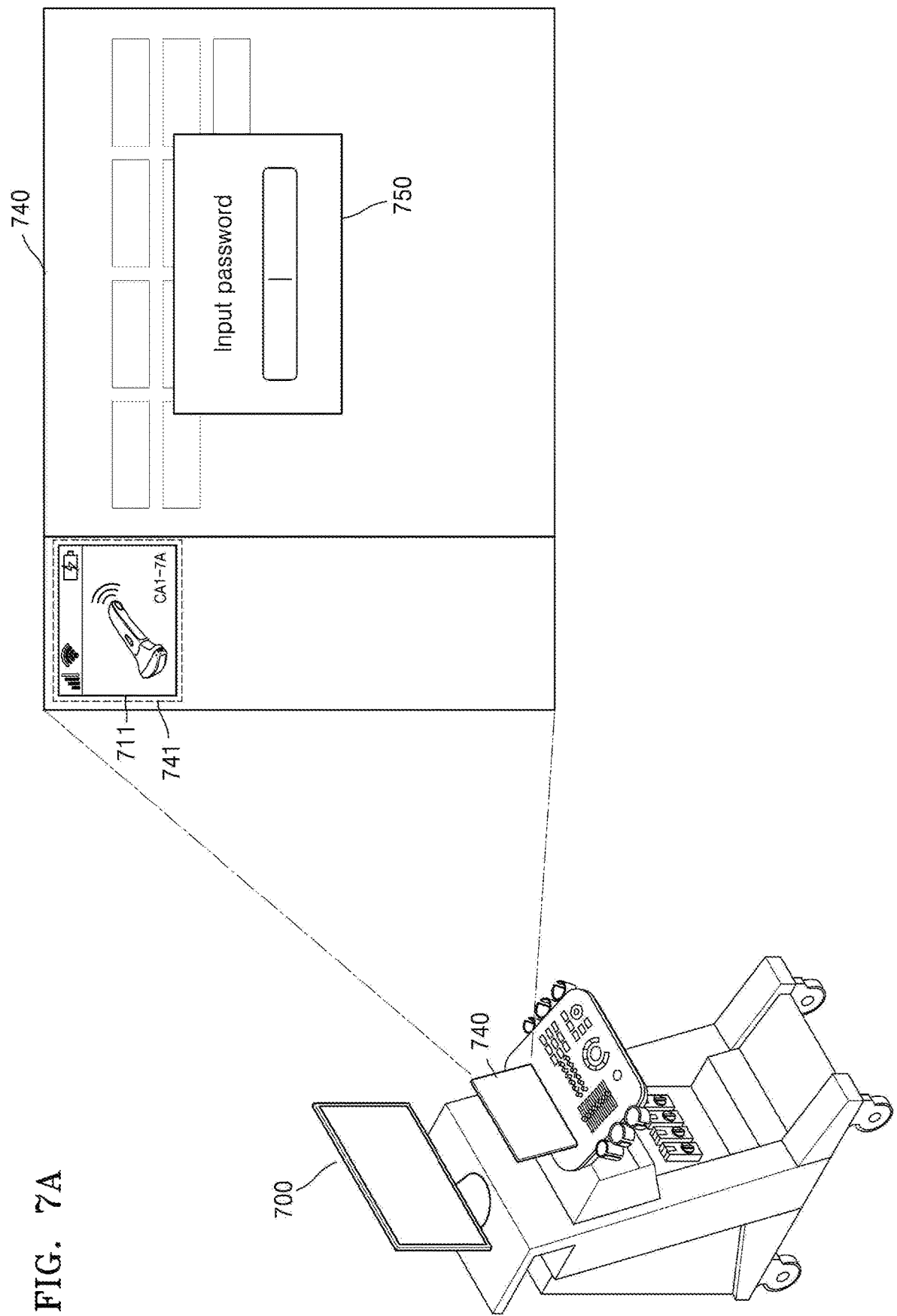
FIGS. 7A and 7B are diagrams for explaining methods, performed by an ultrasound imaging apparatus, of pairing with a wireless ultrasound probe by receiving a password from a user, according to embodiments.
Figure 7B:
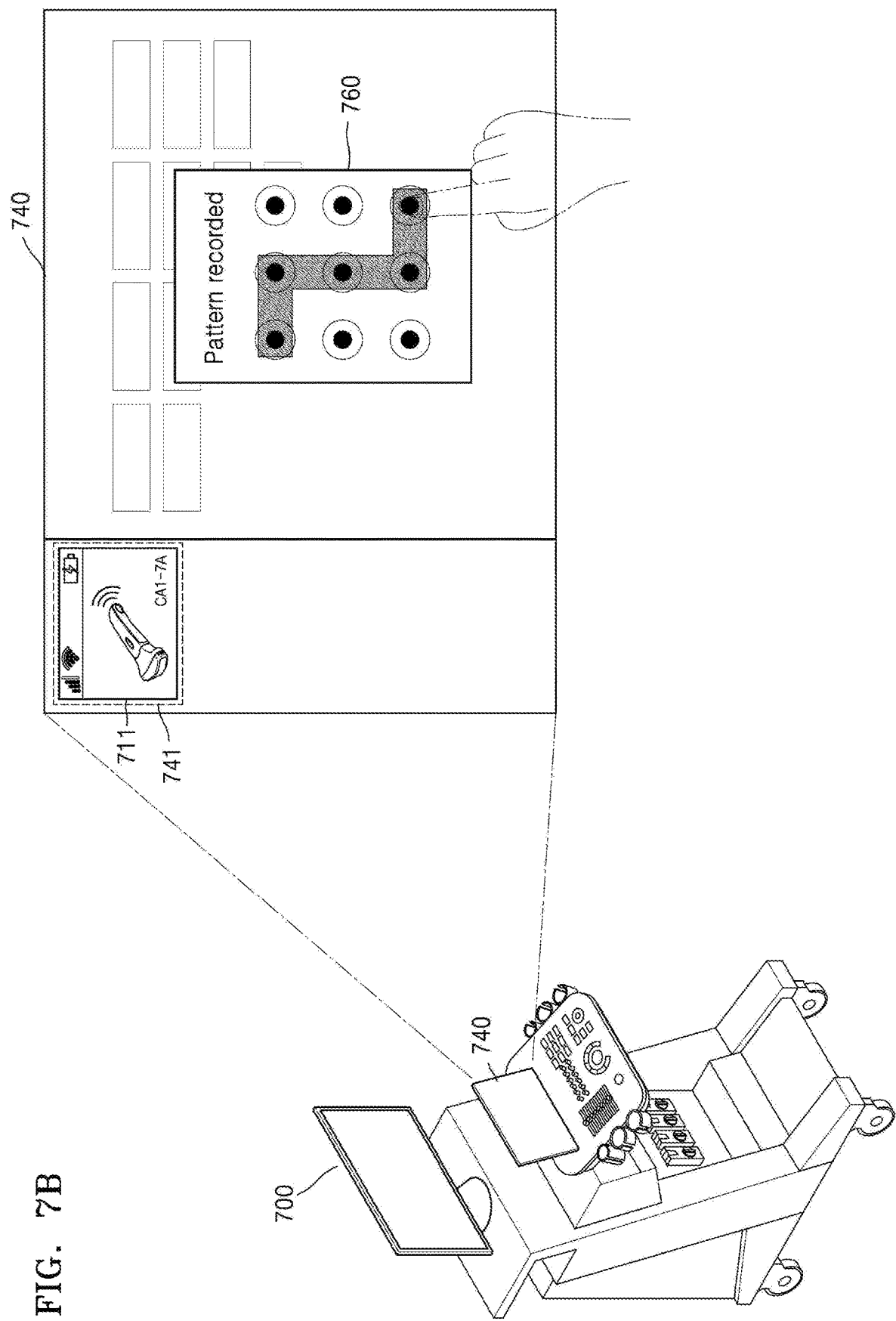

FIGS. 7A and 7B are diagrams for explaining methods, performed by an ultrasound imaging apparatus 700, of pairing with a wireless ultrasound probe by receiving a password from a user, according to embodiments.

Referring to FIG. 7A, the ultrasound imaging apparatus 700 may receive a user input of entering a password. A display 740 of the ultrasound imaging apparatus 700 may display in a first region 741 a thumbnail image 711 of a wireless ultrasound probe to which a charging power is being supplied via a power supply terminal. When the wireless ultrasound probe is being charged, the ultrasound imaging apparatus 700 may display a password UI 750 requesting a user to enter a password on the display 740.

The password is a preset security code that allows the user to use the wireless ultrasound probe that is coupled to the ultrasound imaging apparatus 700 and is being charged and may be composed of letters, numerals, or any combination thereof. The ultrasound imaging apparatus 700 may receive a password from the user via a user input device including at least one of a key pad, a mouse, a trackball, a touch pad, a touch screen, and a jog switch. When the display 740 is formed as a touch screen, the display 740 may be integrated with a touch pad to display a keypad UI including letters and numerals and receive a user touch input for entering a password via the keypad UI.

The ultrasound imaging apparatus 700 may be paired wirelessly with a wireless ultrasound probe only when a password received from the user matches a security code predetermined with respect to the wireless ultrasound probe. Furthermore, the ultrasound imaging apparatus 700 may use the wireless ultrasound probe paired wirelessly thereto to transmit ultrasound signals to an object and receive ultrasound echo signals reflected from the object to thereby acquire ultrasound image data with respect to the object. When the password received from the user does not match the security code predetermined with respect to the wireless ultrasound probe, the ultrasound imaging apparatus 700 may prevent a charging power from being supplied to the wireless ultrasound probe.

Referring to FIG. 7B, an ultrasound imaging apparatus 700 may display in a first region 741 of a display 740 a thumbnail image 711 of a wireless ultrasound probe to which a charging power is being supplied via a power supply terminal. The ultrasound imaging apparatus 700 may receive a user input of entering a specific pattern on the display 740. When the wireless ultrasound probe is being charged, the ultrasound imaging apparatus 700 may display a pattern UI 760 requesting a user to enter a specific pattern on the display 740. In an embodiment, the display 740 may be formed as a touch screen, and receive a user input of touching specific positions on the pattern UI 760 and sequentially dragging over the specific positions.

The ultrasound imaging apparatus 700 may be paired wirelessly with a wireless ultrasound probe only when a specific pattern received from the user matches a pattern preset with respect to the wireless ultrasound probe. Furthermore, the ultrasound imaging apparatus 700 may use the wireless ultrasound probe paired wirelessly thereto to transmit ultrasound signals to an object and receive ultrasound echo signals reflected from the object to thereby acquire ultrasound image data with respect to the object.

When the specific pattern received from the user does not match the pattern preset with respect to the wireless ultrasound probe, the ultrasound imaging apparatus 700 may prevent a charging power from being supplied to the wireless ultrasound probe.

Figure 7C:
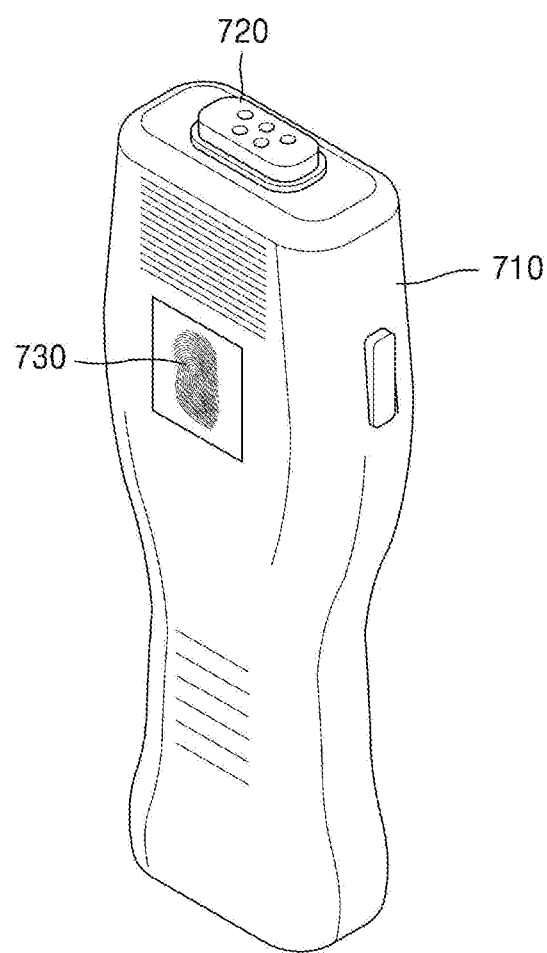
FIG. 7C is a perspective view of a wireless ultrasound probe according to an embodiment.

FIG. 7C is a perspective view of a wireless ultrasound probe 710 according to an embodiment.

Referring to FIG. 7C, the wireless ultrasound probe 710 may include a charging terminal connector 720 and a fingerprint information acquisitor 730 that are respectively provided on sides of the wireless ultrasound probe 710. Since the charging terminal connector 720 corresponds to the charging terminal connectors (210 of FIG. 2A and 220 of FIG. 2B) described with reference to FIGS. 2A and 2B, a detailed description thereof will be omitted here.

The fingerprint information acquisitor 730 may recognize a fingerprint possessed by a user of the wireless ultrasound probe 710 and transmit information about the recognized fingerprint to a controller of the wireless ultrasound probe 710. When information about the fingerprint recognized by the fingerprint information acquisitor 730 matches information about a fingerprint preregistered as an authorized user of the wireless ultrasound probe 710, the wireless ultrasound probe 710 may be paired wirelessly to the ultrasound imaging apparatus (700 of FIGS. 7A or 7B). Furthermore, in an embodiment, when information about the fingerprint recognized by the fingerprint information acquisitor 730 matches information about a fingerprint preregistered as an authorized user of the wireless ultrasound probe 710, the wireless ultrasound probe 710 may be unlocked to transmit ultrasound signals to an object and receive ultrasound echo signals reflected from the object.

When information about the fingerprint recognized by the fingerprint information acquisitor 730 does not match information about a fingerprint preregistered with respect to the wireless ultrasound probe 710, the wireless ultrasound probe 710 switches back to a locked state such that all operations thereof are stopped.

Although FIG. 7C shows that the wireless ultrasound probe 710 includes the fingerprint information acquisitor 730, embodiments are not limited thereto. In an embodiment, the wireless ultrasound probe 710 may include a biometric recognition module for recognizing a user's iris or facial contour.

Figure 8:
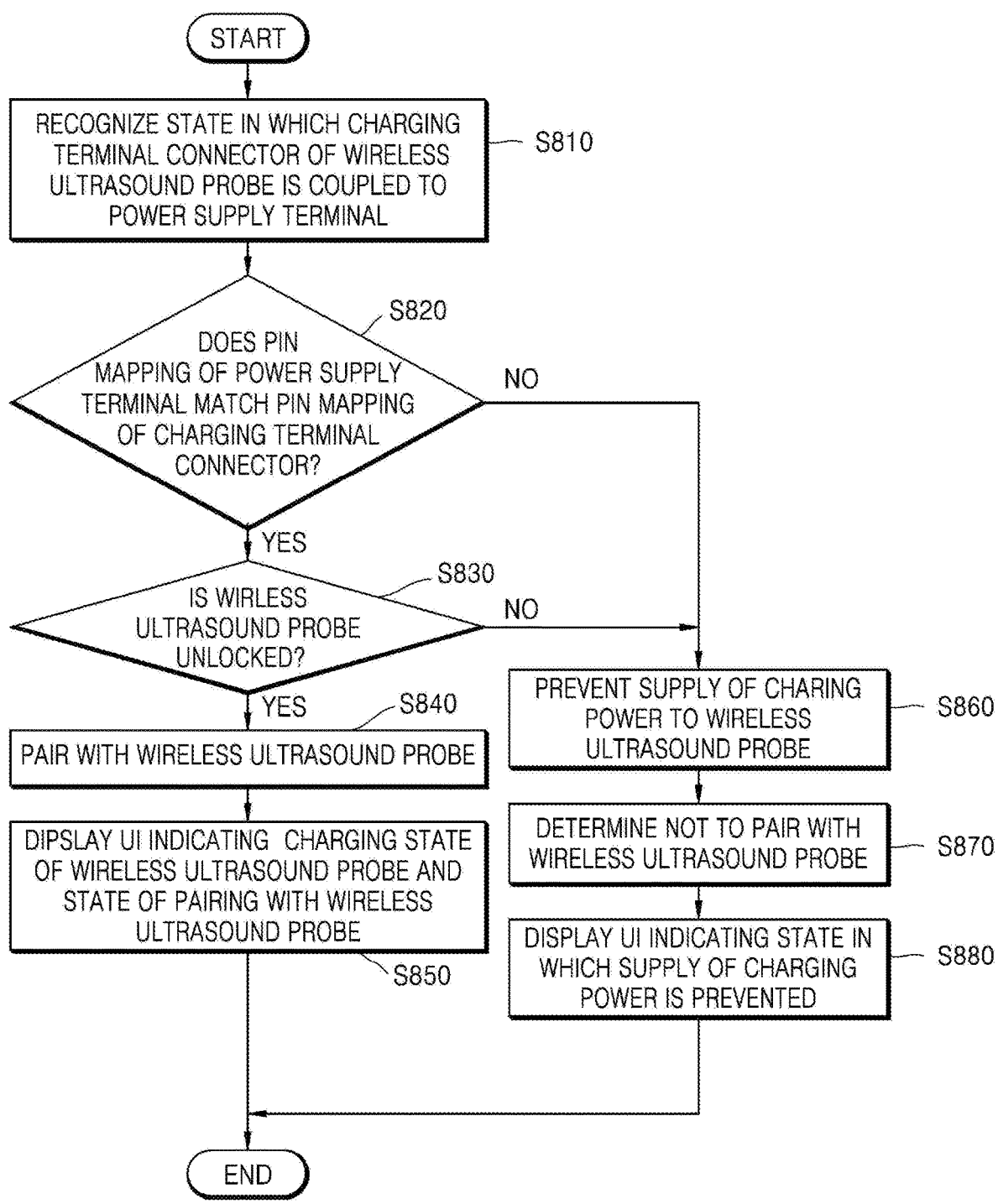
FIG. 8 is a flowchart of a method, performed by an ultrasound imaging apparatus, of determining whether to pair with a wireless ultrasound probe and displaying a state of pairing with the wireless ultrasound probe; according to an embodiment.

FIG. 8 is a flowchart of a method, performed by an ultrasound imaging apparatus, of determining whether to pair with a wireless ultrasound probe and displaying a state of pairing with the wireless ultrasound probe; according to an embodiment.

The ultrasound imaging apparatus recognizes a state in which a charging terminal connector of the wireless ultrasound probe is coupled to a power supply terminal (S810). In an embodiment, the power supply terminal of the ultrasound imaging apparatus may have a unique shape enabling it to be coupled only to the wireless ultrasound probe including the charging terminal connector having a predetermined shape. In an embodiment, the ultrasound imaging apparatus may recognize whether pin mapping of the power supply terminal is identical to pin mapping of the charging terminal connector of the wireless ultrasound probe.

The ultrasound imaging apparatus checks whether pin mapping of the power supply terminal is identical to pin mapping of the charging terminal connector (S820). Even when the charging terminal connector of the wireless ultrasound probe is physically coupled to the power supply terminal of the ultrasound imaging apparatus in operation S810, the pin mapping of the power supply terminal may be different from that of the charging terminal connector. In an embodiment, pin mapping of the charging terminal connector of the wireless ultrasound probe may be set to receive a charging power only via the specific power supply terminal of the ultrasound imaging apparatus.

When the pin mapping of the power supply terminal of the ultrasound imaging apparatus is identical to the pin mapping of the charging terminal connector of the wireless ultrasound probe in operation S820, the ultrasound imaging apparatus may supply a charging power to the wireless ultrasound probe. Otherwise, when the pin mapping of the power supply terminal of the ultrasound imaging apparatus does not match the pin mapping of the charging terminal connector of the wireless ultrasound probe in operation S820, the ultrasound imaging apparatus may prevent a charging power from being supplied to the wireless ultrasound probe.

The ultrasound imaging apparatus determines whether the wireless ultrasound probe is unlocked (S830). In operation S830, "unlocked" may mean that the wireless ultrasound probe is paired with the ultrasound imaging apparatus by using a wireless communication method even when a charging power is supplied to the wireless ultrasound probe and authorization is granted to use the wireless ultrasound probe to acquire ultrasound image data with respect to the object. Matching of the pin mappings with each other in operation S820 is a primary unlock operation for using the wireless ultrasound probe. Operation S830 may be a secondary unlock operation for pairing with the wireless ultrasound probe being charged and acquiring ultrasound image data.

In an embodiment, the ultrasound imaging apparatus may receive a password or specific pattern with respect to the wireless ultrasound probe from the user and determine whether to pair with the wireless ultrasound probe being charged based on the received password or specific pattern. The ultrasound imaging apparatus may wirelessly pair with the wireless ultrasound probe only when the password received from the user matches a security code predetermined with respect to the wireless ultrasound probe (S840).

According to an embodiment, the ultrasound imaging apparatus may receive ID information and characteristic information of the wireless ultrasound probe being charged and determine whether to pair with the wireless ultrasound probe based on the received ID information and the characteristic information of the wireless ultrasound probe. In operation S830, the ID information may refer to an ID and a type of the wireless ultrasound probe, and the characteristic information may be information including at least one of a wireless communication frequency used for wireless communication with the ultrasound imaging apparatus, a connection type, an executable application, a wireless communication method, a communication status, battery charging information, a remaining battery capacity, and a remaining usability time.

The ultrasound imaging apparatus may wirelessly pair with the wireless ultrasound probe only when the received ID information and characteristic information of the wireless ultrasound probe respectively match ID information and characteristic information predetermined by the ultrasound imaging apparatus to enable pairing (S840).

In an embodiment, the ultrasound imaging apparatus may acquire biometric information including at least one of a fingerprint, an iris, and a facial contour of a user of the wireless ultrasound probe and identify the user based on the acquired biometric information. The ultrasound imaging apparatus may determine whether to pair with the wireless ultrasound probe according to the biometric information of the identified user. In an embodiment, the wireless ultrasound probe may include a biometric recognition module configured to acquire biometric information including at least one of a user's fingerprint, iris, and facial contour. The wireless ultrasound probe may determine to wirelessly pair with the ultrasound imaging apparatus only when biometric information acquired by the biometric recognition module matches biometric information predetermined to authorize the use of the wireless ultrasound probe (S840).

The ultrasound imaging apparatus pairs with the wireless ultrasound probe (S840). In an embodiment, the ultrasound imaging apparatus may transmit a pairing signal to the wireless ultrasound probe unlocked in operation S830 and wirelessly connect with the wireless ultrasound probe. In an embodiment, the ultrasound imaging apparatus may be paired with the wireless ultrasound probe by using at least one of wireless communication methods including a WLAN, Wi-Fi, Bluetooth, Zigbee, WFD, IrDA, BLE, NFC, WiBro, WiMAX, SWAP, WiGig, and RF communication.

The ultrasound imaging apparatus displays a UI indicating a charging state of the wireless ultrasound probe and a state of pairing with the wireless ultrasound probe (S850), as will be described in more detail below with reference to FIG. 9A.

The ultrasound imaging apparatus prevents a charging power from being supplied to the wireless ultrasound probe (S860). The ultrasound imaging apparatus may prevent power from being supplied to the wireless ultrasound probe when the pin mapping of the power supply terminal does not match the pin mapping of the charging terminal connector of the wireless ultrasound probe in operation S820 or when it is not determined in operation S830 that the wireless ultrasound probe is unlocked.

The ultrasound imaging apparatus determines not to pair with the wireless ultrasound probe (S870). When the ultrasound imaging apparatus does not pair with the wireless ultrasound probe, the wireless ultrasound probe cannot apply an ultrasound signal to the object or receive an ultrasound echo signal reflected from the object. Thus, it becomes impossible to use the wireless ultrasound probe.

The ultrasound imaging apparatus displays a UI indicating a state in which supply of a charging power is prevented (S880). In an embodiment, the ultrasound imaging apparatus may display on a display a UI indicating a state in which supply of a charging power is prevented and that pairing with the wireless ultrasound probe is impossible, as will be described in more detail below with reference to FIG. 9B.

Figure 9A:
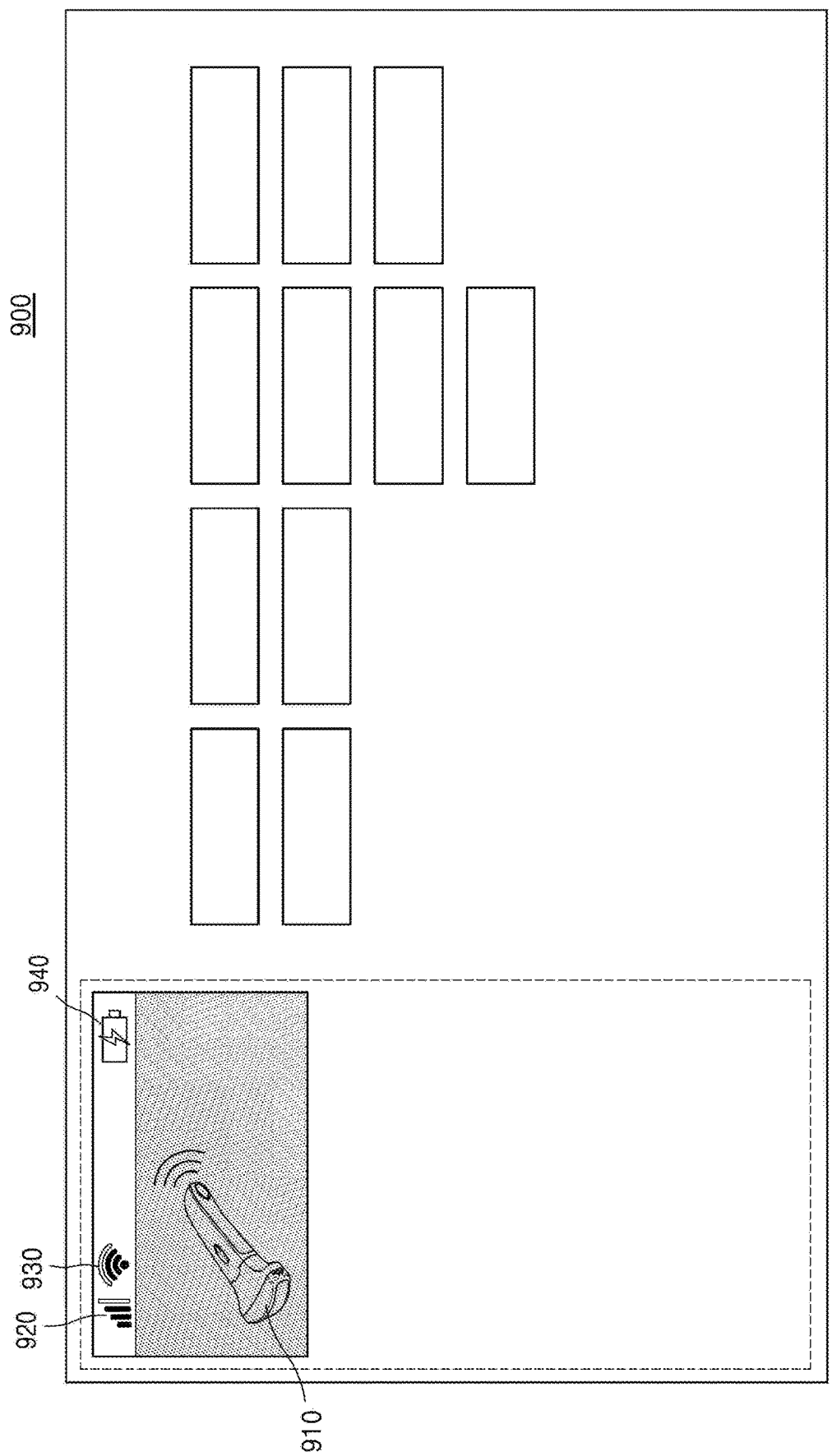

FIGS. 9A and 9B are diagrams for explaining methods by which an ultrasound imaging apparatus displays states of pairing with wireless ultrasound probes, according to embodiments.

Referring to FIG. 9A, a display 900 of the ultrasound imaging apparatus may display a thumbnail image 910 of a wireless ultrasound probe that is paired thereto by using a wireless communication method and UIs related to wireless pairing, a communication status, a communication method, battery charging, etc. As a component of the ultrasound imaging apparatus, the display 900 may be attached to a control panel to display a UI, but embodiments are not limited thereto. According to an embodiment, the display 900 may also display an ultrasound image of an object generated based on ultrasound image data produced by the wireless ultrasound probe. The display 900 may display UIs used for operating the ultrasound imaging apparatus, e.g., for obtaining an ultrasound image of the object or manipulating the obtained ultrasound image by using the ultrasound imaging apparatus.

A region in which the thumbnail image 910 of the wireless ultrasound probe is displayed may be shown in a certain color of shade to distinguish the region from the remaining regions. This may indicate that the wireless ultrasound probe is paired with the ultrasound imaging apparatus. An UI indicating status information of the wireless ultrasound probe may be displayed at the top of the region in which the thumbnail image 910 of the wireless ultrasound probe is displayed. In an embodiment, the UI may be a GUI graphically representing the status information. The UI displayed on the display 900 may include a first UI 920 indicating a status of wireless connection between the wireless ultrasound probe and the ultrasound imaging apparatus, a second UI 930 indicating a wireless communication method used to pair the wireless ultrasound probe with the ultrasound imaging apparatus, and a third UI 940 indicating a state in which a charging power is being supplied to the wireless ultrasound probe. In an embodiment, the display 900 may display ID information of the wireless ultrasound probe paired wirelessly to the ultrasound imaging apparatus. In the embodiment shown in FIG. 9A, the wireless ultrasound probe paired with the ultrasound imaging apparatus may be L3-12W.

The first UI 920 may be a UI indicating a wireless connection status as the number of bar-shaped antennas. The more bars in the first UI 92 may mean the smoother wireless connection.

The second UI 930 may be a UI composed of symbols indicating Wi-fi, Bluetooth, NFC, WiGig, etc. and may represent a wireless communication method used to pair the wireless ultrasound probe with the ultrasound imaging apparatus. In FIG. 9A, the number of bars in the first UI 920 and the number of antennas in the second UI 930 may be UIs that graphically represent a status of wireless communication between the wireless ultrasound probe and the ultrasound imaging apparatus. For example, in the second UI 930 indicating pairing via Wi-fi, the more antennas that are filled in a fan-shaped antenna symbol may mean the smoother Wi-fi pairing between the wireless ultrasound probe and the ultrasound imaging apparatus.

The third UI 940 may be a UI indicating that the wireless ultrasound probe receives a charging power from a power supply terminal of the ultrasound imaging apparatus and is charging a battery embedded therein.

According to the embodiment shown in FIG. 9A, the first through third UIs 920, 930, and 940 displayed on the display 900 may allow the user to easily identify status information of the wireless ultrasound probe paired with the ultrasound imaging apparatus, thereby increasing user convenience.

Referring to FIG. 9B, although the display 900 of the ultrasound imaging apparatus displays a thumbnail image 911 of a wireless ultrasound probe, the wireless ultrasound probe represented by the thumbnail image 911 may be a wireless ultrasound probe that is not paired with the ultrasound imaging apparatus. Unlike in FIG. 9A, a region in which the thumbnail image 911 of the wireless ultrasound probe is displayed is not shown in a certain color or shade, which means that the wireless ultrasound probe is not paired with the ultrasound imaging apparatus.

Even when a charging terminal connector of the wireless ultrasound probe is physically coupled to the power supply terminal of the ultrasound imaging apparatus, pin mapping of the power supply terminal may not match pin mapping of the charging terminal connector (S820 of FIG. 8), or the wireless ultrasound probe may not be unlocked (S830 of FIG. 8). In this case, a charging power may be prevented from being supplied to the wireless ultrasound probe, and the wireless ultrasound probe may not be paired with the ultrasound imaging apparatus.

A first UI 921 displayed on the display 900 maybe a UI indicating a state in which the wireless ultrasound probe is not connected wirelessly to the ultrasound imaging apparatus. Signal bars displayed in the first UI 921 are empty, which means wireless connection is not made between the wireless ultrasound probe and the ultrasound imaging apparatus.

A second UI 931 indicates a wireless communication method used to pair the wireless ultrasound probe with the ultrasound imaging apparatus. However, since the wireless ultrasound probe is currently not being paired with the ultrasound imaging apparatus, fan-shaped signal bars displayed in the second UI 931 are all empty.

A third UI 941 may be a UI indicating a state in which a charging power is not being supplied to the wireless ultrasound probe. The third UI 941 indicates that supply of power from the ultrasound imaging apparatus to the wireless ultrasound probe is prevented. In other words, even though the wireless ultrasound probe is physically coupled to the ultrasound imaging apparatus, an electrical connection is not actually made therebetween, and thus, power supply and charging cannot be performed and thus pairing is terminated. To restore pairing with the wireless ultrasound probe, the wireless ultrasound probe has to be electrically connected to the ultrasound imaging apparatus and receive a charging power therefrom.

According to the embodiment shown in FIG. 9, the display 900 of the ultrasound imaging apparatus displays UIs indicating a state in which the wireless ultrasound probe is not paired wirelessly to the ultrasound imaging apparatus and is not being charged. This may allow the user to quickly identify a status of the wireless ultrasound probe, thereby increasing user convenience.

Figure 10:
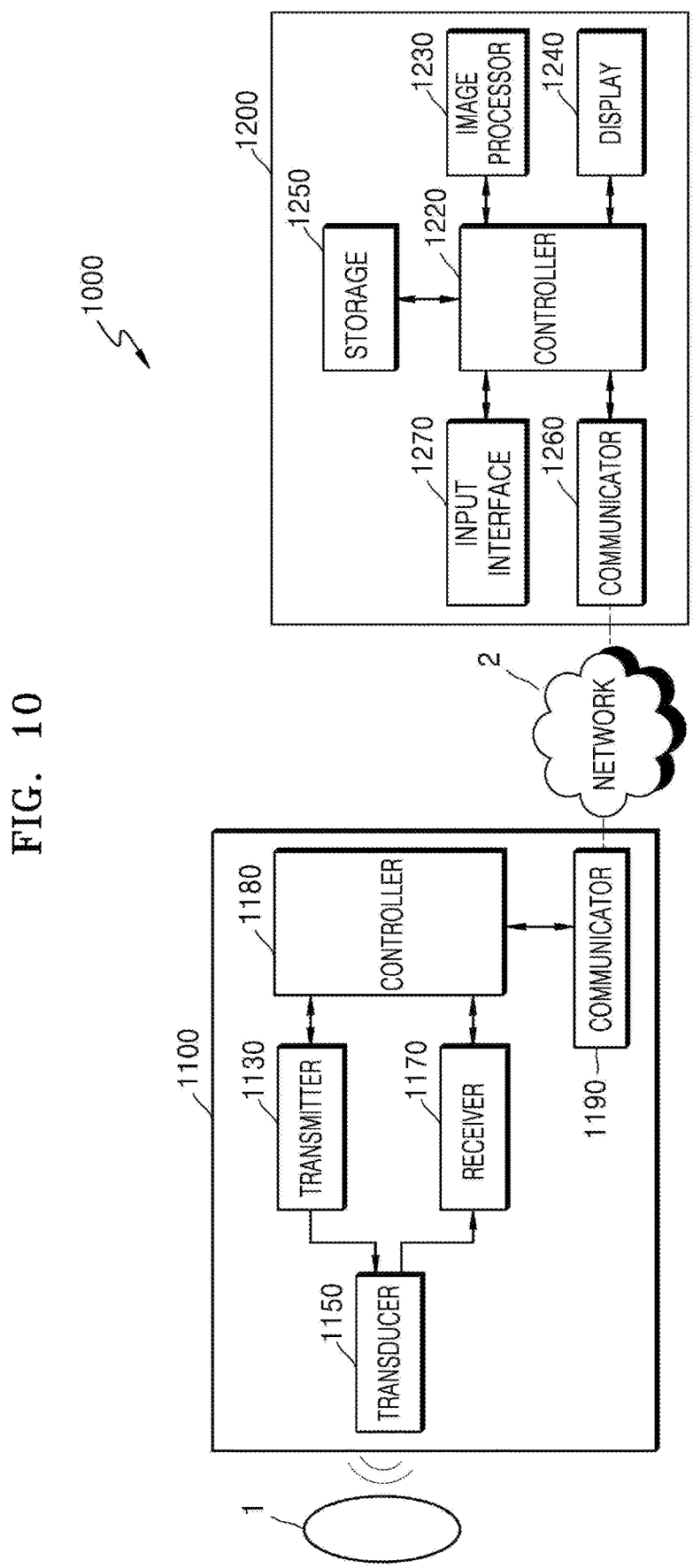
FIG. 10 is a block diagram of a configuration of an ultrasound system including a wireless ultrasound probe and an ultrasound imaging apparatus, according to an embodiment.

FIG. 10 is a block diagram of a configuration of an ultrasound system 1000 including a wireless ultrasound probe 1100 and an ultrasound imaging apparatus 1200, according to an embodiment.

Referring to FIG. 10, the ultrasound system 1000 may include the wireless ultrasound probe 1100 and the ultrasound imaging apparatus 1200.

The wireless ultrasound probe 1100 may include a transmitter 1130, a transducer 1150, a receiver 1170, a controller 1180, and a communicator 1190. Although FIG. 10 shows that the wireless ultrasound probe 1100 includes both the transmitter 1130 and the receiver 1170, according to an implemented configuration, the wireless ultrasound probe 1100 may include some of the components of the transmitter 1130 and the receiver 1170 while the ultrasound diagnosis apparatus 1200 may also include some of them.

The transducer 1150 may include a plurality of transducer elements. The plurality of transducer elements transmit ultrasound signals to an object 1 in response to transmitting signals received from the transmitter 1130. The transducer elements may receive ultrasound signals reflected from the object 1 to generate reception signals.

The controller 1180 controls the transmitter 1130 to generate transmitting signals to be respectively applied to the transducer elements based on a position and a focal point of the transducer elements.

The controller 1180 controls the receiver 1170 to generate ultrasound data by performing analog-to-digital conversion on the reception signals received from the transducer 1150 and summing the analog-to-digital converted reception signals based on a position and a focal point of the transducer elements.

The communicator 1190 may wirelessly transmit the generated ultrasound data or ultrasound image to the ultrasound diagnosis apparatus 1200 via a wireless network. Alternatively, the communicator 240 may receive a control signal and data from the ultrasound diagnosis apparatus 1200.

In addition, the ultrasound system 1000 may also include at least one wireless ultrasound probe 1100 according to the implementation form.

The ultrasound diagnosis apparatus 1200 may receive ultrasound data or an ultrasound image from the wireless ultrasound probe 1100. The ultrasound diagnosis apparatus 1200 may include a controller 1220, an image processor 1230, a display 1240, a storage 1250, a communicator 1260, and an input interface 1270.

The image processor 1230 may generate an ultrasound image by using ultrasound data received from the wireless ultrasound probe 1100.

The display 1240 may display an ultrasound image received from the wireless ultrasound probe 1100 and an ultrasound image generated by the ultrasound diagnosis apparatus 1200 and the ultrasound diagnosis system 1000. The ultrasound diagnosis system 1000 may include two or more displays 1240 according to its implemented configuration. Furthermore, the display 1240 may be combined with a touch panel to form a touch screen.

The controller 1220 may control all operations of the ultrasound diagnosis system 1000 and flow of signals between the internal elements of the ultrasound diagnosis system 1000. The controller 1220 may include a memory for storing a program or data to perform functions of the ultrasound diagnosis system 1000 and a processor for processing the program or data. Furthermore, the controller 1220 may control the operation of the ultrasound diagnosis system 1000 by receiving a control signal from the input interface 1270 or an external apparatus.

The ultrasound diagnosis apparatus 1200 may include the communicator 1260 and may be connected to external apparatuses, for example, servers, medical apparatuses, and portable devices such as smart phones, tablet PCs, wearable devices, etc., via the communicator 1260.

The communicator 1260 may include at least one element capable of communicating with the external apparatuses. For example, the communicator 1260 may include at least one of a local area communication module, a wired communication module, and a wireless communication module.

The communicator 1260 may receive a control signal and data from an external apparatus and transmit the received control signal to the controller 1220 such that the controller 1220 may control the ultrasound diagnosis system 1000 in response to the received control signal.

Alternatively, the controller 1220 may transmit a control signal to the external apparatus via the communicator 1260 to control the external apparatus in response to the control signal from the controller 1220.

For example, the external apparatus may process data from the external apparatus in response to the control signal from the controller 1220 received via the communicator 1260.

A program for controlling the ultrasound diagnosis system 1000 may be installed in the external apparatus. The program may include command languages for performing part of operation of the controller 1220 or the entire operation thereof.

The program may be pre-installed in the external apparatus or may be installed by a user of the external apparatus by downloading the program from a server that provides applications. The server that provides applications may include a recording medium on which the program is stored.

The storage 1250 may store various data or programs for driving and controlling the ultrasound diagnosis system 1000, input and/or output ultrasound data, ultrasound images, etc.

The input interface 1270 receives a user input for controlling the ultrasound diagnosis system 1000. For example, the user input may include an input for manipulating a button, a keypad, a mouse, a trackball, a jog switch, or a knop, an input for touching a touchpad or a touch screen, a voice input, a motion input, and an input of biometric information such as iris recognition or fingerprint recognition, but embodiments are not limited thereto.

Examples of the ultrasound diagnosis apparatus 1200 according to an embodiment will now be described in detail with reference to FIGS. 11A through 11C.

FIGS. 11A, 11B, and 11C are diagrams illustrating ultrasound diagnosis apparatus according to an exemplary embodiment.

Referring to FIGS. 11A and 11B, the ultrasound diagnosis apparatuses 1000a and 1000b may include a main display 1310 and a sub-display 1320. At least one among the main display 1310 and the sub-display 1320 may include a touch screen. The main display 1310 and the sub-display 1320 may display ultrasound images and/or various information processed by the ultrasound diagnosis apparatuses 1000a and 1000b. The main display 1310 and the sub-display 1320 may provide graphical user interfaces (GUI), thereby receiving user's inputs of data to control the ultrasound diagnosis apparatuses 1000a and 1000b. For example, the main display 1310 may display an ultrasound image and the sub-display 1320 may display a control panel to control display of the ultrasound image as a GUI. The sub-display 1320 may receive an input of data to control the display of an image through the control panel displayed as a GUI. The ultrasound diagnosis apparatuses 1000a and 1000b may control the display of the ultrasound image on the main display 1310 by using the input control data.

Referring to FIG. 11B, the ultrasound diagnosis apparatus 1000b may include a control panel 1340. The control panel 1340 may include buttons, trackballs, jog switches, or knobs, and may receive data to control the ultrasound diagnosis apparatus 1000b from the user. For example, the control panel 1340 may include a time gain compensation (TGC) button 1331 and a freeze button 1332. The TGC button 1331 is to set a TGC value for each depth of an ultrasound image. Also, when an input of the freeze button 1332 is detected during scanning an ultrasound image, the ultrasound diagnosis apparatus 1000b may keep displaying a frame image at that time point.

The buttons, trackballs, jog switches, and knobs included in the control panel 1340 may be provided as a GUI to the main display 1310 or the sub-display 1320.

Referring to FIG. 11C, the ultrasound diagnosis apparatus 1000c may include a portable device. An example of the portable ultrasound diagnosis apparatus 1000c may include, for example, smart phones including probes and applications, laptop computers, personal digital assistants (PDAs), or tablet PCs, but an exemplary embodiment is not limited thereto.

The ultrasound diagnosis apparatus 1000c may include the probe 2000 and a main body 1400. The probe 2000 may be connected to one side of the main body 1400 by wire or wirelessly. The main body 1400 may include a touch screen 1450. The touch screen 1450 may display an ultrasound image, various pieces of information processed by the ultrasound diagnosis apparatus 1000c, and a GUI.

The embodiments of the present disclosure can be written as computer programs and can be implemented in general-use digital computers that execute the programs using a computer-readable recording medium. The command language may be stored in the form of a program code, and when executed by a processor, the command language may generate a certain program module and perform certain operations. In addition, the command language may, when executed by a processor, may perform certain operations described in the embodiments disclosed in the present disclosure.

Examples of the computer-readable recording medium include magnetic storage media (e.g., ROM, floppy disks, hard disks, etc.), optical recording media (e.g., CD-ROMs or DVDs), etc.

While the present disclosure has been particularly shown and described with reference to exemplary embodiments thereof, it will be understood by those of ordinary skill in the art that various changes in form and details may be made therein without departing from the spirit and scope of the present disclosure as defined by the following claims.

What is claimed is:

1. A wireless ultrasound probe connected wirelessly to an ultrasound imaging apparatus, the wireless ultrasound probe comprising:
a battery;
a charging terminal connector that is coupled to a power supply terminal of the ultrasound imaging apparatus and receives power from the power supply terminal to charge the battery;
a wireless communication module; and
a controller configured to control the wireless communication module to transmit identification information and characteristic information to the ultrasound imaging apparatus,
wherein the charging terminal connector has a unique shape configured to be physically coupled to the power supply terminal,
wherein the charging terminal connector has a shape corresponding to a shape of the power supply terminal such that the charging terminal connector is coupled only to the predetermined power supply terminal of the ultrasound imaging apparatus,
wherein the wireless communication module is paired with the ultrasound imaging apparatus based on the identification information and characteristic information of the wireless ultrasound probe, and
wherein the characteristic information of the wireless ultrasound probe includes at least one of a wireless communication frequency used for communication, a connection type, an executable application, a wireless communication method, a communication status, battery charging information, a remaining battery capacity, and a remaining usability time.

2. The wireless ultrasound probe of claim 1, wherein the charging terminal connector comprises a plurality of pins that are coupled to the power supply terminal and is pin mapped such that at least one of the plurality of pins receives power from the power supply terminal.

3. The wireless ultrasound probe of claim 2, wherein the charging terminal connector is pin mapped to have a combination of at least two of the plurality of pins via which the power is received from the power supply terminal.

4. The wireless ultrasound probe of claim 1,
wherein the controller is further configured to recognize a battery charging state in which the charging terminal connector is physically coupled to the power supply terminal such that power is applied to the battery, and control, when the wireless ultrasound probe is in the battery charging state, the wireless communication module to be paired wirelessly to the ultrasound imaging apparatus by using a wireless communication method.

5. The wireless ultrasound probe of claim 4, further comprising a biometric recognition module configured to acquire biometric information including at least one of a user's fingerprint, iris, and facial contour, wherein the controller is further configured to identify the user based on the biometric information acquired by the biometric recognition module and control the wireless communication module to be paired with the ultrasound imaging apparatus by using a wireless communication method according to the identified user.

6. An ultrasound imaging apparatus connected wirelessly with a wireless ultrasound probe, the ultrasound imaging apparatus comprising:
a wireless communication module;
a power supply terminal that is coupled to a charging terminal connector of the wireless ultrasound probe to supply a charging power for charging a battery of the wireless ultrasound probe;
a sensor configured to recognize a charging state in which the power supply terminal is physically coupled with the charging terminal connector of the wireless ultrasound probe such that power is supplied to the battery; and
a controller configured to control the wireless communication module to pair the ultrasound imaging apparatus with the wireless ultrasound probe that is recognized by the sensor as being in the charging state by using a wireless communication method,
wherein the power supply terminal has a unique shape configured to be physically coupled only with the wireless ultrasound probe including the charging terminal connector having a predetermined shape,
wherein the controller is further configured to control the wireless communication module to receive idenification information and characteristic information of the wireless ultrasound probe coupled to the power supply terminal and determine whether to pair the ultrasound imaging apparatus with the wireless ultrasound probe based on the received identification information and characteristic information of the wireless ultrasound probe, and
wherein the characteristic information of the wireless ultrasound probe includes at least one of a wireless communication frequency used for communication, a connection type, an executable application, a wireless communication method, a communication status, battery charging information, a remaining battery capacity, and a remaining usability time.

7. The ultrasound imaging apparatus of claim 6, further comprising a user input interface configured to receive a password or a specific pattern from a user,
wherein the controller is further configured to determine, when the charging state is recognized, whether to pair the ultrasound imaging apparatus with the wireless ultrasound probe based on the received password or specific pattern.

8. The ultrasound imaging apparatus of claim 6, further comprising a display configured to display a user interface (UI) indicating the charging state of the wireless ultrasound probe and a state of pairing with the wireless ultrasound probe.

9. The ultrasound imaging apparatus of claim 6, wherein the power supply terminal comprises a plurality of pins and is pin mapped such that at least one of the plurality of pins supplies power to the wireless ultrasound probe via the charging terminal connector,
wherein the sensor is further configured to recognize whether pin mapping of the power supply terminal matches pin mapping of the charging terminal connector, and wherein the controller is further configured to determine whether to pair the ultrasound imaging apparatus with the wireless ultrasound probe, based on a result of the recognizing by the sensor as to whether the pin mapping of the power supply terminal matches the pin mapping of the charging terminal connector.

10. The ultrasound imaging apparatus of claim 9, wherein the controller is further configured to prevent the power supply terminal from supplying power to the wireless ultrasound probe when the pin mapping of the power supply terminal does not match the pin mapping of the charging terminal connector.

11. The ultrasound imaging apparatus of claim 10, further comprising a display configured to display a user interface (UI) indicating a state in which the power is prevented from being supplied to the wireless ultrasound probe.

12. A method of connecting an ultrasound imaging apparatus with a wireless ultrasound probe, the method comprising:
recognizing a state in which a charging terminal connector of the wireless ultrasound probe is coupled to a power supply terminal of the ultrasound imaging apparatus;
supplying power to the wireless ultrasound probe coupled to the power supply terminal to charge a battery of the wireless ultrasound probe;
pairing the ultrasound imaging apparatus with the wireless ultrasound probe being charged, by using a wireless communication method;
receiving identification information and characteristic information of the wireless ultrasound probe being charged,
wherein the power supply terminal has a unique shape configured to be physically coupled only with the wireless ultrasound probe including the charging terminal connector having a predetermined shape,
wherein the pairing of the ultrasound imaging apparatus with the wireless ultrasound probe comprises determining whether to pair the ultrasound imaging apparatus with the wireless ultrasound probe based on the received identification information and characteristic information of the wireless ultrasound probe, and
wherein the characteristic information of the wireless ultrasound probe includes at least one of a wireless communcation frequency used for communication, a connection type, and executable application, a wireless communication method, a communication status, battery charging information, a remaining battery capacity, and a remaining usability time.

13. The method of claim 12, further comprising receiving a password or a specific pattern from a user,
wherein the pairing of the ultrasound imaging apparatus with the wireless ultrasound probe comprises determining, based on the received password or specific pattern, whether to pair the ultrasound imaging apparatus with the wireless ultrasound probe being charged.

14. The method of claim 12, further comprising acquiring biometric information including at least one of a fingerprint, an iris, and a facial contour of a user of the wireless ultrasound probe,
wherein the pairing of the ultrasound imaging apparatus with the wireless ultrasound probe comprises:
identifying the user based on the acquired biometric information; and
determining whether to pair the ultrasound imaging apparatus with the wireless ultrasound probe according to the identified user.

15. The method of claim 12, further comprising displaying a user interface (UI) indicating a state in which the wireless ultrasound probe is charged and a state in which the wireless ultrasound probe is paired with the ultrasound imaging apparatus.

16. The method of claim 12, further comprising:
recognizing whether pin mapping of the power supply terminal matches pin mapping of the charging terminal connector;
preventing the power from being supplied to the wireless ultrasound probe when the pin mapping of the power supply terminal does not match the pin mapping of the charging terminal connector; and
displaying a user interface (UI) indicating a state in which the power is prevented from being supplied to the wireless ultrasound probe.

* * * * *

UNITED STATES PATENT AND TRADEMARK OFFICE
CERTIFICATE OF CORRECTION

PATENT NO. : 11,627,939 B2
APPLICATION NO. : 16/226925
DATED : April 18, 2023
INVENTOR(S) : Joonghyun Park et al.

Page 1 of 1

It is certified that error appears in the above-identified patent and that said Letters Patent is hereby corrected as shown below:

In the Claims

In Claim 6, Column 25, Line 31, delete "idenification" and insert -- identification --

In Claim 12, Column 26, Line 45, delete "communcation" and insert -- communication --

Signed and Sealed this
Seventeenth Day of June, 2025

Coke Morgan Stewart
*Acting Director of the United States Patent and Trademark Office*